(12) United States Patent
Abramson et al.

(10) Patent No.: US 8,834,946 B2
(45) Date of Patent: Sep. 16, 2014

(54) SYSTEM AND METHOD FOR DETECTION OF A CONTAMINATED BEVERAGE

(75) Inventors: Michael T. Abramson, Boston, MA (US); John C. MacDonald, Jefferson, MA (US)

(73) Assignee: Drinksavvy, Inc., Boston, MA (US)

( * ) Notice: Subject to any disclaimer, the term of this patent is extended or adjusted under 35 U.S.C. 154(b) by 191 days.

(21) Appl. No.: 13/404,663

(22) Filed: Feb. 24, 2012

(65) Prior Publication Data
US 2012/0164279 A1 Jun. 28, 2012

Related U.S. Application Data

(63) Continuation of application No. PCT/US2011/001521, filed on Aug. 29, 2011, which is a continuation of application No. 13/204,708, filed on Aug. 7, 2011, which is a continuation-in-part of application No. 12/977,009, filed on Dec. 22, 2010, now abandoned.

(51) Int. Cl.
*A22C 13/00* (2006.01)
*G01N 21/75* (2006.01)
*G01N 31/22* (2006.01)
*G01N 33/14* (2006.01)

(52) U.S. Cl.
CPC ............ *G01N 31/22* (2013.01); *G01N 33/14* (2013.01)
USPC ............ 426/87; 426/383; 422/408; 422/425; 422/400; 422/430; 436/2

(58) Field of Classification Search
USPC ............ 426/87, 231, 232, 383; 422/400, 408, 422/425, 430; 436/1, 2
See application file for complete search history.

(56) References Cited

U.S. PATENT DOCUMENTS

| 3,450,327 A | 6/1969 | Ludder |
| 3,480,402 A | 11/1969 | Jackson |
| 3,768,978 A | 10/1973 | Grubb et al. |
| 3,876,378 A | 4/1975 | Montagnon |
| 4,168,676 A | 9/1979 | Itoh |

(Continued)

FOREIGN PATENT DOCUMENTS

| GB | 2 418 248 | 3/2006 |
| WO | 96/27795 | 9/1996 |
| WO | 2006/018619 | 2/2006 |
| WO | WO 2009006254 A1 * | 1/2009 ............ C09B 69/10 |

OTHER PUBLICATIONS

PCT/US2011/001521 International Search Report and Written Opinion dated Dec. 30, 2011, pp. 1-12.

(Continued)

*Primary Examiner* — Drew Becker
*Assistant Examiner* — Luana Z Long
(74) *Attorney, Agent, or Firm* — Michael T. Abramson; Holland & Knight LLP

(57) ABSTRACT

A system and method for a beverage container configured to test for a contaminated beverage in the beverage container comprises a base of the beverage container, an upper portion of the beverage container, and a sidewall with an inner surface and an outer surface that extends from the base to the upper portion, and a testing material. A portion of the beverage container is the testing material configured to visibly react when the portion of the beverage container is contacted with the contaminated beverage.

28 Claims, 19 Drawing Sheets

(56) References Cited

U.S. PATENT DOCUMENTS

| | | | |
|---|---|---|---|
| 5,154,448 | A | 10/1992 | Griffin et al. |
| 5,456,754 | A | 10/1995 | Matheson et al. |
| 5,869,341 | A | 2/1999 | Woodaman |
| 6,153,147 | A | 11/2000 | Craig |
| 6,156,431 | A | 12/2000 | Kitchen et al. |
| 6,620,626 | B1 | 9/2003 | Bodily |
| 6,703,216 | B2 | 3/2004 | Parsons et al. |
| 2001/0046710 | A1 | 11/2001 | Cutler |
| 2002/0192722 | A1 | 12/2002 | Stolowitz et al. |
| 2003/0026731 | A1 | 2/2003 | Peter |
| 2003/0111003 | A1 | 6/2003 | Engelman et al. |
| 2004/0096569 | A1 | 5/2004 | Barkalow et al. |
| 2004/0121420 | A1 | 6/2004 | Smith |
| 2004/0146429 | A1* | 7/2004 | Guerra et al. .............. 422/56 |
| 2005/0101771 | A1 | 5/2005 | Kouzuma et al. |
| 2005/0153452 | A1* | 7/2005 | Williams et al. ............. 436/2 |
| 2006/0144730 | A1 | 7/2006 | Greenberg |
| 2007/0065338 | A1 | 3/2007 | Schindler et al. |
| 2007/0083009 | A1 | 4/2007 | Chai |
| 2007/0099300 | A1 | 5/2007 | Cordani et al. |
| 2008/0006600 | A1 | 1/2008 | Greenbert |
| 2008/0102482 | A1 | 5/2008 | Grossman et al. |
| 2009/0197297 | A1 | 8/2009 | Murray et al. |
| 2009/0266290 | A1 | 10/2009 | Sliwa et al. |
| 2010/0041078 | A1 | 2/2010 | Bendinskas et al. |
| 2010/0081188 | A1 | 4/2010 | Campbell et al. |
| 2010/0160556 | A1 | 6/2010 | Wallrapp et al. |
| 2010/0197516 | A1 | 8/2010 | Holmes |
| 2010/0248334 | A1 | 9/2010 | McDaniel |
| 2011/0165687 | A1* | 7/2011 | Grossman et al. ............. 436/20 |
| 2012/0160725 | A1 | 6/2012 | Abramson |
| 2012/0164278 | A1 | 6/2012 | Abramson et al. |

OTHER PUBLICATIONS

1001 Ideas for Kitchen Organization: The Ultimate Source Book for Storage, by Joseph R. Provey. 2007. p. 22.

International Preliminary Report on Patentability for PCT/US2011/001521 mailed Jul. 4, 2013.

Jordan et al., "Surface-Initiated Anionic Polymerization of Styrene by Means of Self-Assembled Monolayers," Contribution from the Dept. of Chemical Engineering, J.Am. Chem. Soc. 121(5) p. 1016-1022 (Jan. 22, 1999).

* cited by examiner

SYSTEM AND METHOD FOR DETECTION OF A CONTAMINATED BEVERAGE

RELATED CASES

This application is a continuation of International Application No. PCT/US2011/001521 with an international filing date of Aug. 29, 2011, which is a continuation of U.S. patent application Ser. No. 13/204,708 filed on Aug. 7, 2011, which is a continuation-in-part of U.S. patent application Ser. No. 12/977,009 filed on Dec. 22, 2010 by Michael T. Abramson, titled SYSTEM AND METHOD FOR DETECTION OF A CONTAMINATED BEVERAGE, the contents of which are all hereby incorporated by reference.

FIELD OF THE DISCLOSURE

The present disclosure relates generally to contamination detection, and, more particularly, to detecting when a beverage has been contaminated.

BACKGROUND OF THE DISCLOSURE

Drug facilitated sexual assaults are a ubiquitous problem. Commonly known as "date rape", the sexual assault generally occurs while the victim is incapacitated due to unknowingly imbibing chemical substances (i.e., drugs) surreptitiously placed in the victim's beverage by an assailant. Some common drugs associated with date rape are, e.g., Rohypnol, Ketamine, GHB (Gamma-Hydroxybutyrate), GBL (Gamma Butyrolactone), and 1,4-butanediol. Once ingested, the chemicals may act rapidly in the human body, often within 20 minutes, causing physical and psychological symptoms such as disinhibition, muscle relaxation, passivity, and loss of will to resist an assailant.

There are known techniques for detecting when a victim has ingested such drugs. For example, Woods et al., *Journal of Chromatography*, A 2004, 1056: 83-90, describes a system for simultaneous analysis of GHB and its precursors in urine using liquid chromatography-tandem mass spectrometry. Though this and similar techniques may be effective, a disadvantage is that they are not practical for non-professionals, and they require expensive equipment. Another disadvantage is the reactive nature of the test, meaning the system is testing the urine, thus the drugs have already been ingested and the victim may have already been assaulted before testing is even contemplated.

Other testing devices, such as those described in U.S. patent application Ser. No. 10/583,512 filed on Dec. 16, 2004 by Grossman et al., titled APPARATUS FOR DETECTING DRUGS IN A BEVERAGE, and in U.S. Pat. No. 6,153,147 issued on Nov. 28, 2000 by Craig, titled BEVERAGE ANALYSIS SAMPLE, provide a more immediate and proactive approach through early detection. For example, Craig discloses a test apparatus utilized by the user at the site and time of beverage consumption. A portion of the beverage must first be captured by the user and drawn into an analysis chamber where the beverage is subjected to a chemical reagent composition, where the results of a color assay are viewable. That is, a color change may indicate a drug has been placed in the beverage.

Other testing devices may use the proactive techniques, but also provide discretion when testing a beverage for contamination. For example, the testing device described by Greenberg in U.S. patent application Ser. No. 11/899,646 filed on Sep. 7, 2007, titled STRAW HOLDER INTEGRATED WITH A BEVERAGE CONTAINER, shows a testing material that a user may utilize to test the beverage. Notably, the testing material is part of an entirely separate component which itself must then be connected to a beverage container.

A more discrete testing apparatus can be found in U.S. patent application Ser. No. 10/761,066 filed on Jan. 20, 2004 by Guerra et al., titled APPARATUS AND METHOD FOR TESTING A BEVERAGE FOR A CLANDESTNE ILLICIT SUBSTANCE. Hiding the test strips allows the user to test the beverage without embarrassment by onlookers. For example, Guerra describes camouflaging and/or hiding individual drug testing strips in such things as a cocktail napkin, a beverage coaster, a placemat, a menu, a match book, a drink carrier (e.g., used to carry multiple drinks at once), a flyer, a coupon, and even a business card. As another example, the testing apparatus described in U.S. patent application Ser. No. 11/266,690 filed on Nov. 3, 2005 by Cordani et al., titled LIQUID TEST PROBE, is camouflaged as a drinking straw. Notably, the disguised drinking straw only functions as a test device and not as an actual straw. Yet another example can be found in U.S. patent application Ser. No. 12/150,505 filed on Apr. 28, 2008 by Sliwa et al., titled BUOYANT-CAPABLE BEVERAGE AND FOOD CONTENT-SENSOR, describing a separate floating device in a beverage where the testing material is located. To test the beverage, the user must first remove a sample of the beverage and place it on the test portion of the device.

However, the prior art suffers from numerous disadvantages. For example, regardless of how quick a test result is determined, or how discreetly a testing apparatus may be hidden, the responsibility to carry the testing apparatus on oneself is burdensome and rests solely on the user. Moreover, even if a beverage has been tested at time $T_1$, there is no assurance that the beverage subsequently has not been contaminated at time $T_2$. Thus, there is an additional requirement for the user to continuously test and re-test the beverage and to have the user bring enough testing material to do so. Testing and re-testing the beverage is not only a hassle, but remembering to do so may become more difficult as time progresses (e.g., due to increased alcohol consumption). Additionally, as more alcohol is consumed, a user may be less able to distinguish between the normal effect of an alcoholic beverage and the effect of a contaminated alcoholic beverage. Accordingly, there remains a need for a more convenient, effortless, and continuous system to detect if and when a beverage has been contaminated.

SUMMARY OF THE DISCLOSURE

The present disclosure overcomes the disadvantages of the prior art by providing a system and method for detection of a contaminated beverage, e.g., by using the beverage container itself (e.g., a drinking cup) as a testing material. For example, in one embodiment, the inside portion of the beverage container which is used to hold the beverage is also the testing material that may visibly alert, signal, or otherwise react when contacted with a drug that is mixed in the beverage (e.g., Rohypnol, Ketamine, GHB (Gamma-Hydroxybutyrate), GBL (Gamma Butyrolactone), 1,4-butanediol, etc.). The reaction, e.g., color change, may then rapidly alert the user that the beverage in the beverage container is contaminated before too much, if any, of the contaminated beverage has been consumed.

In another embodiment, the testing material of the beverage container may be coated or lined with a film (e.g., wax). For example, if the testing material is part of the inside of the beverage container, the wax film may prevent the beverage contained within the beverage container from immediately contacting and reacting with the testing material. Thus, should the user desire to test the beverage for contaminants, the user need only, e.g., "scratch" away or otherwise remove the protective wax lining, thereby exposing the newly revealed testing material inside the beverage container to any potential contaminants in the beverage held in the beverage container. In such an embodiment, the beverage container advantageously provides multiple locations for individual testing by scratching away the wax film from different locations as desired. In alternative embodiments, the wax lining may be a type of semi permeable membrane or other similar material used to provide a delay from when the beverage is placed in the beverage container and when the beverage and any contaminants mixed therein eventually permeate through the lining to make contact with the testing material where a reaction may be seen. Thus, it is possible that little or no action is required by the user to test or re-test the beverage.

Advantageously, by using the beverage container itself as the testing material, the user is provided with a (near) effortless and continuous monitoring of the beverage within the beverage container without such illustrative burdens required by the prior art, such as, inter alia, remembering to bring a testing kit (disguised or otherwise) with a sufficient number of testing strips, remembering to test the beverage, and remembering to re-test the beverage at different times. As another advantage, even if the user cannot distinguish between the effect of the alcohol and the effect of ingesting a contaminated beverage, other onlookers may still notice the reaction of the beverage container (i.e., the testing material) and provide a warning to the user.

BRIEF DESCRIPTION OF THE DRAWINGS

The above and further advantages of the disclosure may be better understood by referring to the following description in conjunction with the accompanying drawings in which like reference numerals indicate identically or functionally similar elements, of which.

DETAILED DESCRIPTION OF AN ILLUSTRATIVE EMBODIMENT

Drug Testing

Figure 1:
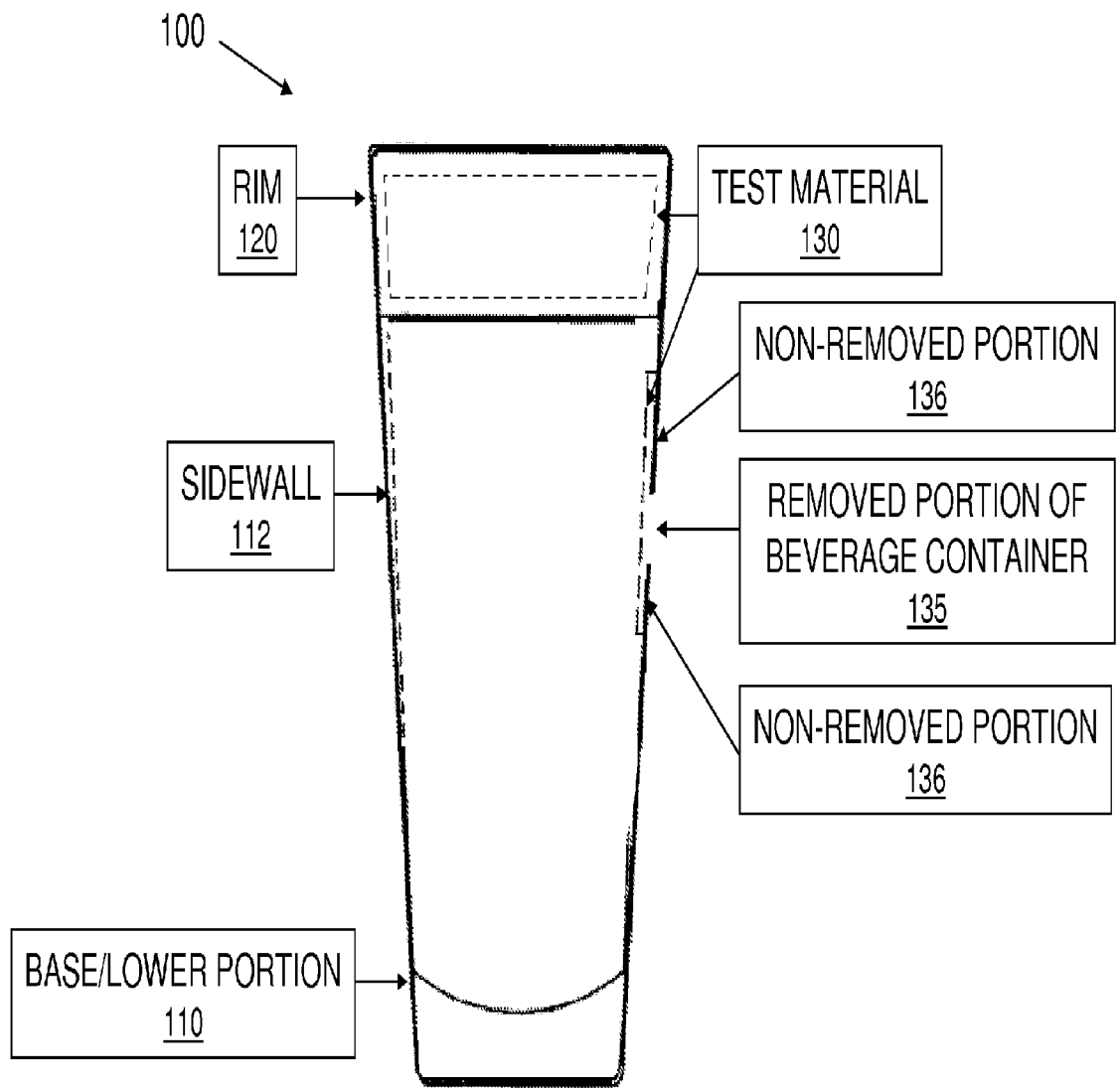
FIG. 1 is a schematic block diagram of an illustrative beverage container that may be used in accordance with the present disclosure.

As can be appreciated by those skilled in the art, there are well known techniques and testing materials that may be used to detect the presence of drugs in a liquid. For example, as noted above with reference to U.S. Pat. No. 6,153,147, a device or testing strip may comprise one or more reagent indicators deposited on an absorptive carrier (e.g., filtration paper). Different reagent indicators may be used for detecting different drugs. For example, flunitrazepam, which is commonly known as Rohypnol or "Ruffies", is a member of a class of compounds known as benzodiazepines. A reaction with Zimmermann's reagent, or a reaction with a platinum/potassium iodide test system, for example, can illustratively detect this class of compound. 4-Hydroxybutanoic acid, also known as gamma hydroxy butyrate (GHB), is a commonly known anesthetic. GHB can illustratively be identified in a reaction system with, e.g., bromo cresol purple. Ketamine is another anesthetic which can illustratively be identified using, e.g., cobalt thiocyanate. Those skilled in the art will recognize that other reagent indicators suitable for testing a beverage are also contemplated for these drugs and different drugs. As such, the reagent indicators described are exemplary only and should not be taken to limit the scope of the disclosure.

In some testing systems, visual indications from the testing material (e.g., the reagent) may be observed when a drug is detected. One type of visual indicator may be color change. For example, if a sample of a beverage is introduced to a testing area with the reagent, a color change from white to a violet/purple color may be observed at the reagent within 30 seconds or less if Rohypnol is present in the sample. If a violet/purple color is not observed within 30 seconds, the beverage analysis may be considered negative for Rohypnol. As another example, if the sample is introduced to a testing area with a reagent to detect GHB, a color change from white to a yellow/orange color may appear within 30 seconds or less if GHB is not present in the sample. However, if GHB is present, a purple/black color may appear within 30 seconds or less. In a preferred embodiment, any color change would appear in response to detecting the presence of a drug, rather than having a color change appear in response to detecting that the drug is not present. While not required, the preferred embodiment may be helpful to avoid confusion, for example, should the user forget what each color indicates.

Notably, while some examples of reagents and tests are described, those skilled in the art will appreciate that other reagents, tests, color combinations, calorimetric indicators, etc., for similar and/or other drug types are well known in the art and may be used with embodiments of the present disclosure without departing from the scope and spirit of the disclosure. As such, the described detection methods and devices (e.g., color combinations, test strips, particular reagents, etc.) or other functional equivalents that have similar properties capable of carrying out the objectives of the disclosure are contemplated. Accordingly, the specific testing materials described should be taken as exemplary only and not to limit the scope of the disclosure.

Beverage Container

The present disclosure overcomes the disadvantages of the prior art by providing a system and method for detection of a contaminated beverage, e.g., using the beverage container itself as a testing material. That is, at least a portion of the beverage container itself is the testing material. For example, in one embodiment, the inside of the beverage container itself is not only the surroundings of the beverage container that holds the beverage, but the inside of the beverage container itself is also the testing material that may react when contacted with a mixture of the beverage and a drug, such as Rohypnol, Ketamine, GHB (Gamma-Hydroxybutyrate), GBL (Gamma Butyrolactone), 1,4-butanediol, etc. Using the beverage container as the testing material illustratively may be implemented in some embodiments by (i) removing and then replacing a portion of the beverage container with the testing material, (ii) directly attaching the testing material to a portion of the beverage container (with or without removing the portion), or (iii) any combination thereof. The reaction of the testing material, e.g., color change of the beverage container, may then rapidly alert or signal to the user that the beverage in the beverage rage container is contaminated before too much, if any, of the contaminated beverage has been consumed.

According to one embodiment, only select portions of the beverage container, such as the rim or the inside/outside of the beverage container, are lined with the testing material. However, the entirety of the beverage container may also be lined with the testing material. Moreover, it is contemplated that the entirety of the beverage container could be configured as the testing material shaped as the beverage container in an alternative embodiment. In the latter embodiment, it may be necessary to fortify the testing material so as to enable the testing material to act as a beverage container (e.g., to prevent leaking through the testing material). The film described in greater detail below may be used to fortify the testing material. However, other conventional techniques similar to those used on conventional paper or cardboard beverage containers described below may also be used and are well known in the art.

Advantageously, by using the beverage container itself as the testing material (e.g., where the beverage container functions as both a beverage container and as the testing material), the user is provided with a (near) effortless and continuous monitoring of the beverage within the beverage container without such illustrative burdens required by the prior art, such as, inter alia, remembering to bring a testing kit (disguised or otherwise) with a sufficient number of testing strips, remembering to test the beverage, and remembering to re-test the beverage at different times. As another advantage, even if the user cannot distinguish between the effect of an alcoholic beverage and the effect of ingesting a contaminated alcoholic beverage, other onlookers may still notice the reaction of the beverage container and provide a warning to the user. Additionally, the testing material of the beverage container (e.g., any unused portions) may also be used to test other beverages of different users, such as an acquaintance that may not be in possession of either the disclosed beverage container or their own tests.

Figure 6A:
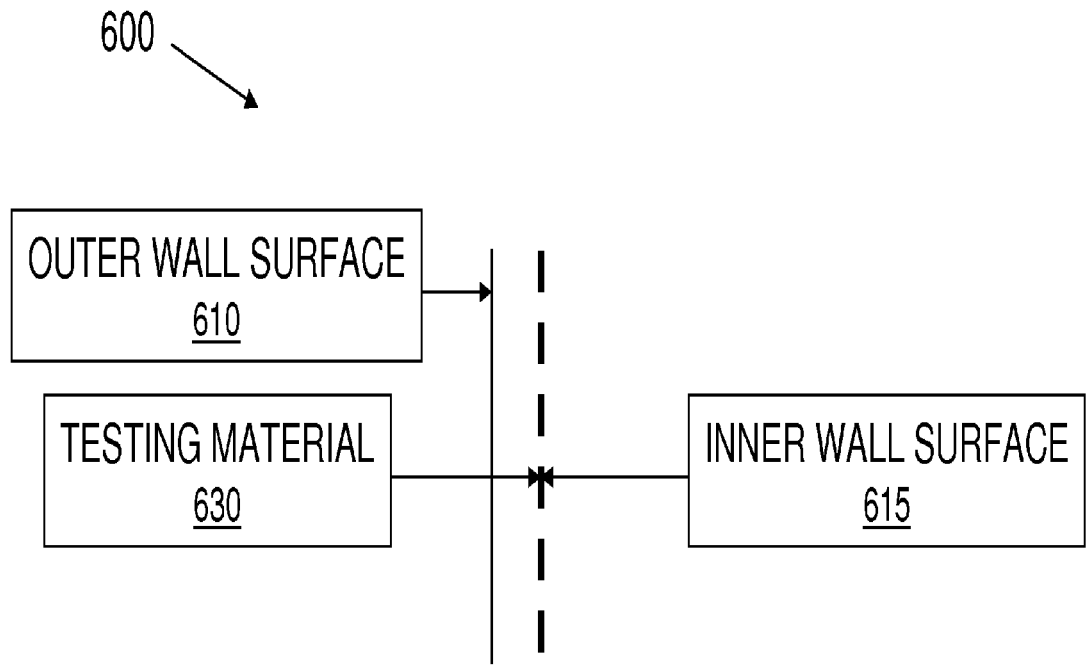
FIG. 6a is a schematic block diagram of an illustrative portion of a beverage container that may be used in accordance with the present disclosure.

FIG. 1 is a schematic block diagram of an illustrative beverage container 100 that may be used in accordance with the present disclosure. As used herein, the term "beverage container" is defined as any conventional container configured to hold a consumable beverage (e.g., soda, water, beer, etc.) from which a user would drink, such as a cup (e.g., disposable, reusable, paper, plastic, etc.), a glass, a mug, a can (e.g., an aluminum can), a bottle (e.g., a soda bottle), etc. Illustratively, in a preferred embodiment, the beverage container may be disposable, such as the kind sold by Solo® Cup Company headquartered in Lake Forest, Ill. The beverage container may comprise a base 110 (e.g., a lower portion), an upper portion which may comprise a rim 120, a sidewall 112, and testing material 130. The testing material illustratively may be affixed to the beverage container using an adhesive or other similar material which is well known in the art; however, any suitable material may be used. In an alternative embodiment, a portion of the beverage container 100 may be removed 135 and then replaced with the testing material (e.g., by directly attaching the testing material to the removed portion using an adhesive). A sidewall 112 with an inner surface and an outer surface may extend from the base to the upper portion. According to one embodiment, the testing material 130 is at least a portion of the beverage container 100 (e.g., the inner surface of the beverage container's base 110 and/or the rim 120, and/or the sidewall 112 as indicated by the dashed lines). This may be further illustrated in FIGS. 6a and 6b where the testing material 630 is shown as the inner wall surface 615. However, the testing material may also be the outer surface of the beverage container or any other portion of the beverage container. However, it is likely that the user may have to be more proactive about testing if the testing material is on the outside of the sidewall, since in some embodiments, the outside wall does not contact the testing material without help from the user. Nonetheless, this situation may be obviated if the testing material is placed on the outer portion of the sidewall where some of that portion has been removed 135. Any descriptions or illustrations used throughout where the testing material is a specific portion of the beverage container (e.g., the inner surface of the sidewall) should be taken as exemplary only.

According to an illustrative embodiment of the present disclosure, the testing material 130 lining the beverage container 100 remains a single color (e.g., white) as a default base color when no illicit drugs, such as those noted above, are detected. As can be appreciated by those skilled in the art, any other color (including clear or transparent) may be used as the default base color. Preferably, the base color is one that will be readily noticeable to the user or other onlookers if the base color should change, even if the user is in a dimly lit area, such as a dance club or a bar. For example, if the beverage container is white, then a positive drug detection color of black may be easier to notice. As can be appreciated, the use of a clear or transparent beverage container may be easier for the user (or an onlooker) to see a color change of the testing material (i.e., the beverage container) than a less transparent beverage container. Advantageously, because the illustrative embodiments of the beverage container functionally are also the testing material, should a drug be introduced to the (alcoholic or non-alcoholic) beverage in the beverage container, the testing material 130 located in the base 110, the rim 120, or the sidewall 112, will automatically (i.e., without a requirement for the user to do anything if the beverage is in the beverage container) contact the beverage and change color to alert the user of the contamination with minimal action, if any, required by the user. This is advantageous as there is little or no need for the user to actively test or re-test the beverage before being warned about the contamination. Thus, the user may be alerted before too much, if any, of the contaminated beverage has been consumed.

Figure 2:
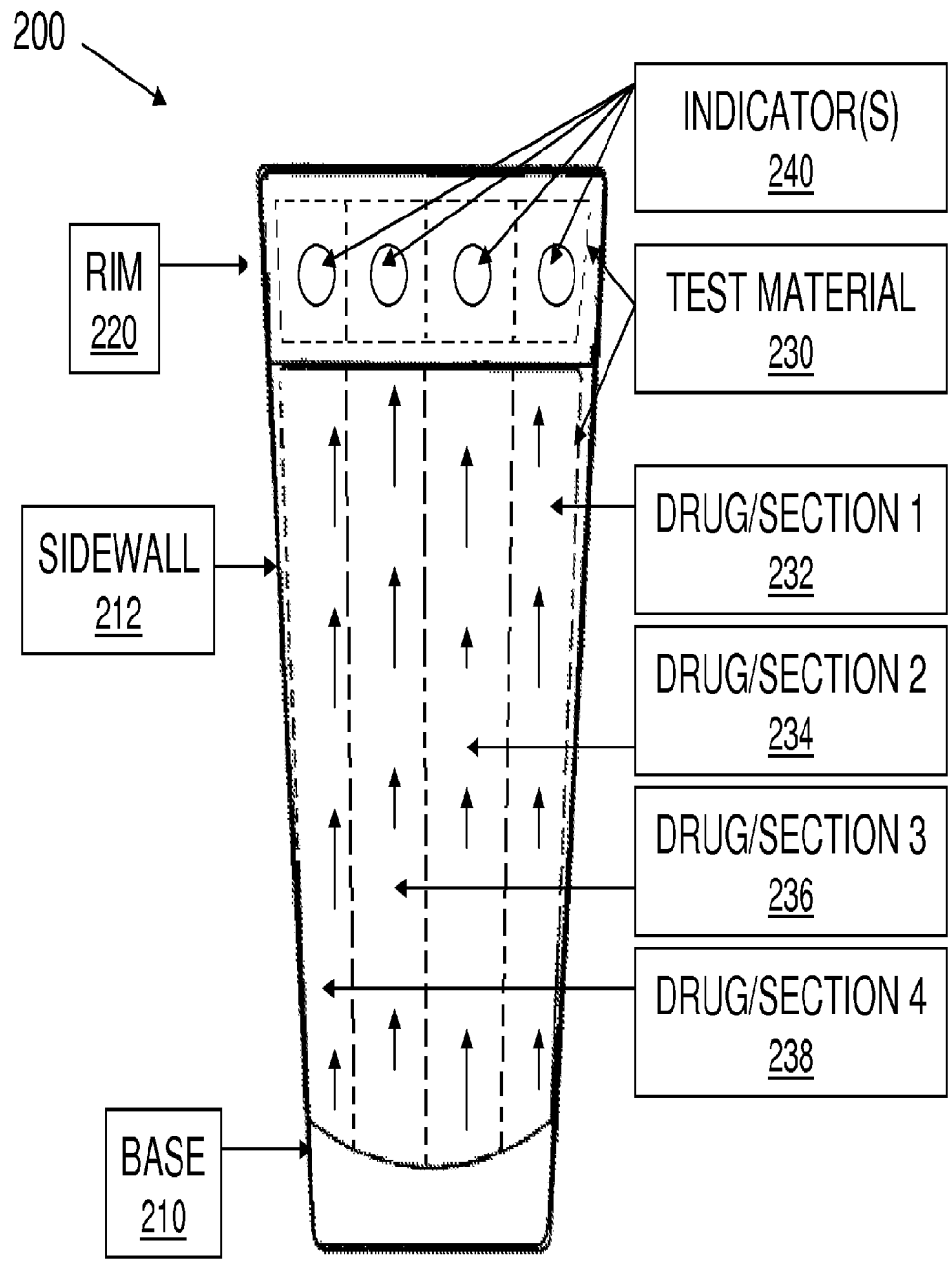
FIG. 2 is a schematic block diagram of an illustrative beverage container that may be used in accordance with the present disclosure.

FIG. 2 is a schematic block diagram of an illustrative beverage container 200 that may be used in accordance with the present disclosure. The beverage container may comprise a base 210, a rim 220, a sidewall 212, and a testing material 230. According to one embodiment, the testing material may be part of the inner/outer lining of the beverage container's base 210, sidewall, or rim 220, as indicated by the dashed lines. According to yet another embodiment, the testing material 230 lining the beverage container may be divided up into different sections (e.g., drug/section 1-4). Each section may comprise a distinct testing material specific to an individual drug. For example, drug/section 232 may be configured to detect GHB, while drug/section 234 may be configured to detect GBL. Accordingly, not only may the user be able to discern that a drug has been introduced to their beverage, but also which drug. Those skilled in the art will appreciate that more or less drug/sections may be used. Those skilled in the art will also appreciate that the drug/sections may be divided other ways besides vertically in any direction or pattern (e.g., horizontal, diagonal, etc.). Thus, the use of only four sections and in any particular configuration should be taken as an example only. In a preferred embodiment, the sections are organized vertically so that the beverage is capable of drug detection regardless of the level of beverage within the beverage container.

In an alternative embodiment, the beverage container 200 may also comprise separate and specific indicators, such as indicator(s) 240. For example, when a particular drug/section detects a drug, the indicator 240 may give an additional warning by changing color on the inside of the beverage container and/or on the outside of the beverage container. Illustratively, this may be accomplished by creating a clear or transparent section specifically for indicators 240, resulting in a distinguishable or otherwise dramatic contrast between the outside of the beverage container (e.g., red) and the indicator 240 (e.g., black). Alternatively, this may be accomplished using a more absorptive testing material that is capable of delivering a sample of the beverage up to the indicators 240.

Figure 3A:
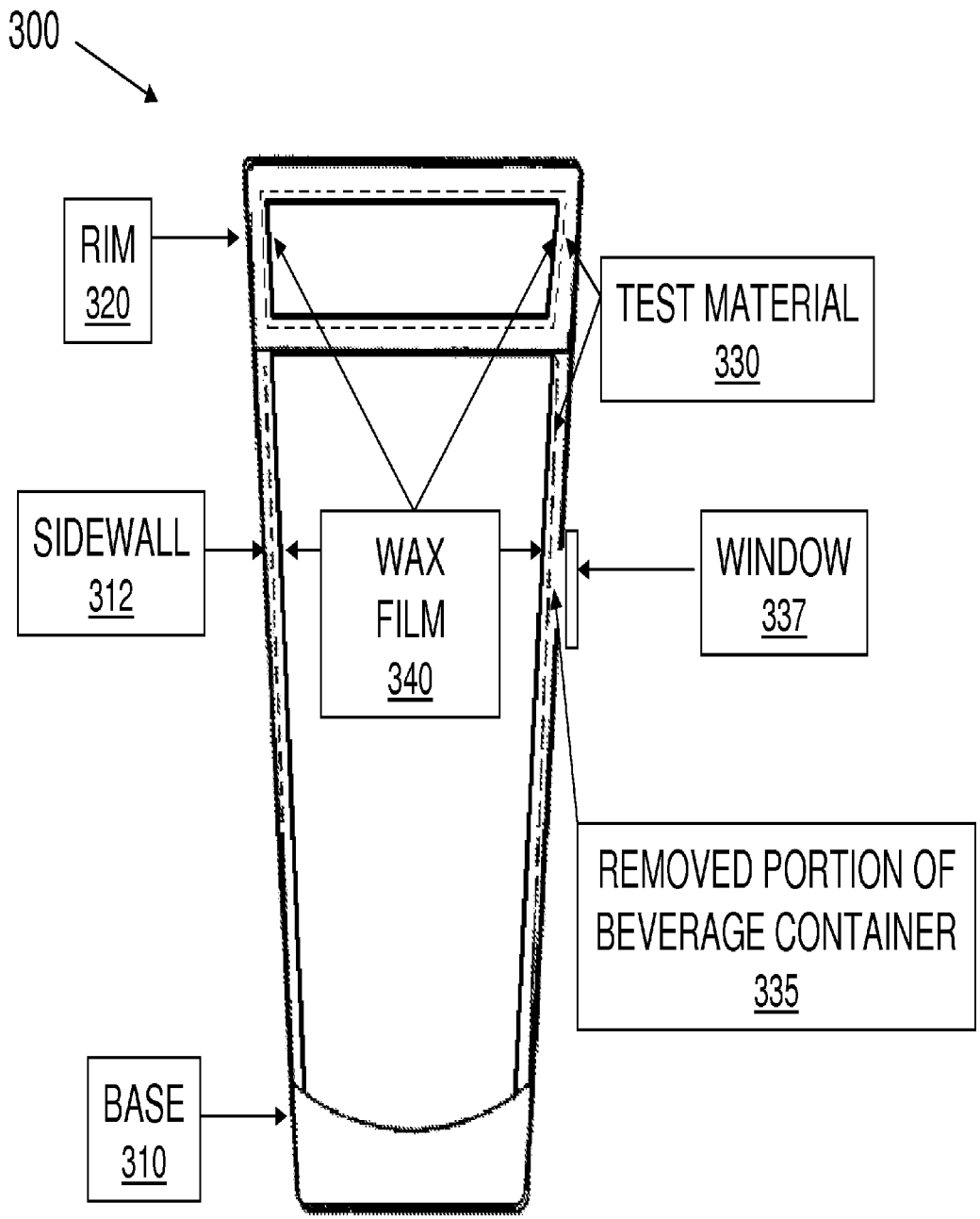
FIG. 3a is a schematic block diagram of an illustrative beverage container with a protective film that may be used in accordance with the present disclosure.

FIG. 3a is a schematic block diagram of an illustrative beverage container 300 with a protective film that may advantageously be used in accordance with the present disclosure. According to one or more illustrative embodiments of the disclosure, the testing material may be coated or coupled with a film (e.g., wax) 340. The wax film may slow or fully prevent the beverage contained within the beverage container from contacting and reacting with the testing material 330 lined, for example, within the inner surface of the base 310 (e.g., lower portion) of the beverage container, the sidewall 312, and/or the rim 320. The film may illustratively comprise a porous substance or other semi permeable material (e.g., membrane) that, over time (e.g., 5 minutes), allows the beverage in the beverage container to pass through the film to contact and react with the testing material. Notably, regardless of how long it takes the beverage to reach the testing material, the time required to notice a reaction (e.g., a color change if the drug is present) may depend on the amount of the beverage relative to the concentration of the drug that is present. According to an alternative embodiment of the disclosure, as noted above, the testing material illustratively may be affixed, united, or otherwise secured to the beverage container using an adhesive, glue, epoxy, or other functional equivalent that has similar properties, before the protective film is applied; however, it is contemplated that the protective film itself may be used in place of or in addition to the adhesive to affix or otherwise secure the testing material to the beverage container. However, any suitable technique or material used to secure the testing material to the beverage container or otherwise make the material of the beverage container comprise the testing material may also be used without departing from the scope and spirit of the disclosure. For example, in an alternative embodiment, a portion of the beverage container 300 may be removed 335 and then replaced with the testing material (e.g., by directly attaching the testing material over the removed portion secured to a non-removed portion 136). In the latter embodiment, it may be beneficial to apply another coating of a liquid resistant wax on the outer most side of the testing material to prevent dripping. Alternatively, a window 337 may be placed over the outer most side of the removed section.

Examples of different wax types and techniques for coating beverage containers are very well known in the art, some of which may be found in, e.g., in U.S. Pat. No. 3,450,327 issued on Jun. 17, 1969 by R. E. Ludder, titled ROUND NESTABLE PAPER CONTAINER HAVING A HIGH GLOSS EXTERIOR FINISH AND AN INTERIOR AND BOTTOM WAX COATED SURFACE, and in U.S. Pat. No. 4,168,676 issued on Sep. 25, 1979 by Itoh, titled APPARATUS FOR MAKING PAPER CONTAINERS, and in U.S. Pat. No. 5,456,754 issued on Oct. 10, 1995 by Matheson et al., titled APPARATUS FOR COATING PAPERBOARD CONTAINERS. For example, Matheson describes directing a relatively narrow spray band of atomized wax towards the interior surfaces of the containers. Matheson goes on to describe that the spray band is volumetrically asymmetrical and is oriented relative to the interior surfaces of the container such that its volumetric asymmetry is directed towards the bottom circumferential seam between a tubular sidewall and bottom wall of the containers. However, those skilled in the art will appreciate that any suitable technique for applying the wax (or other material) to one or more illustrative embodiments of beverage container may be employed without departing from the spirit and scope of the disclosure.

While some examples of the disclosure are discussed using a wax film, those skilled in the art will appreciate that other protective film or coating material may be used. For example, a thermoplastic polymeric material, such as polyethylene, may also be used. Yet another example may be the use of biopolymers, which may generally be described as polymers produced by living organisms. Cellulose, starch, chitin, proteins, and peptides are some examples of biopolymers. Another example of a biopolymer is zein, which is alternatively used as a coating for various foods, such as fruit, to slow the aging process produced by water evaporation. Zein has a number of characteristics that may be valuable for use in the present disclosure. For instance, zein is a natural film-forming polymer, which may provide some of the described resistance to water or other liquid penetration. Zein is also typically non-allergenic and edible. It is also classified as "GRAS" (generally recognized as safe) by the FDA. Those skilled in the art will appreciate that other types of biopolymers or other suitable material capable of carrying out the objectives of the disclosure may also be used without departing from the scope and spirit of the present disclosure. For example, M14-TS, which is well known to those skilled in the art as a water ammonia solution of shellac mixed with Carnauba emulsion and added inerts may also be used.

As will be discussed in greater detail with regard to FIG. 3c, the lining may be removed by the user to expose the testing material to the beverage. As such, another example of the lining material may also be similar to "scratch-off" lottery game pieces, such as the one described in U.S. Pat. No. 5,154,448 issued on Oct. 13, 1992 by Griffin et al., titled SCRATCH-OFF MARKING LABEL. As such, the use of a wax, biopolymer, etc. as the film or coating should not be considered to limit the scope of the disclosure. Those skilled in the art will appreciate that any suitable material (i.e., fluid-impervious or semi-fluid impervious characteristics or functional equivalent that has similar properties) is contemplated that may prevent the beverage contained within the beverage container from immediately contacting and reacting with the testing material of the beverage container (e.g., which may subsequently be readily (e.g., without much difficulty) removed by the user).

Figure 3B:
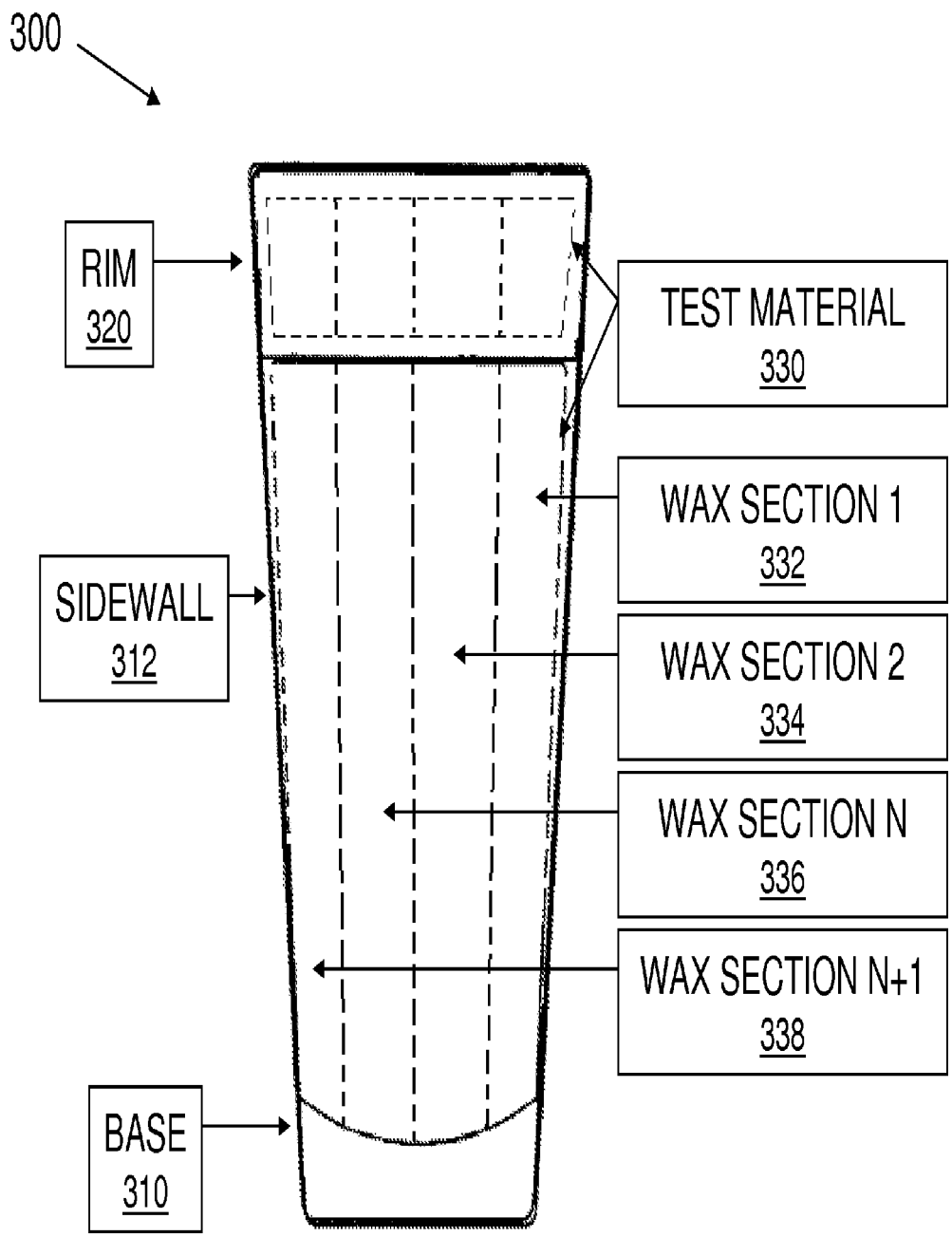
FIG. 3b is a schematic block diagram of an illustrative beverage container with a protective film that may be used in accordance with the present disclosure.

In another embodiment, as seen from FIG. 3b, there may be different types of wax film materials each covering a particular section of the testing material, thereby allowing for varying times when the beverage may pass through the film to the testing material, e.g., depending on the type and thickness of film used. For instance, one section 332 of the testing material may be generally protected (e.g., covered) by a more porous or semi permeable film material that may allow the beverage in the beverage container to pass through the film to the testing material 330 quicker than another section 334 of the testing material 330 that is generally protected by a less porous film material. As such, the beverage container would first "automatically" (i.e., without a need for the user to do anything once the beverage is in the beverage container) "self-test" the beverage at section 332 at a first predetermined time and then "automatically" self "re-test" the beverage at section 334 at a second predetermined time according to how much less porous the film is at each respective section. As can be appreciated by those skilled in the art, other factors in addition to how porous the film is, such as temperature, surface area to volume ratio, etc., may also affect the rate at which the beverage may pass though the film to the testing material. Illustratively, each section may be capable of testing the same drugs (e.g., X, Y, Z), thus, each drug (e.g., X, Y, Z) may be covered by the "re-test" at each section. While only two different rates (e.g., a quicker and a slower rate) are described, those skilled in the art will recognize that any number of different sections 336 and 338 (and different rates) may be used either separately or simultaneously depending on the different types of film used. Thus, the use of only two different rates (for two different types of film) is an example and should not be taken as limiting the scope of the disclosure.

Figure 6B:
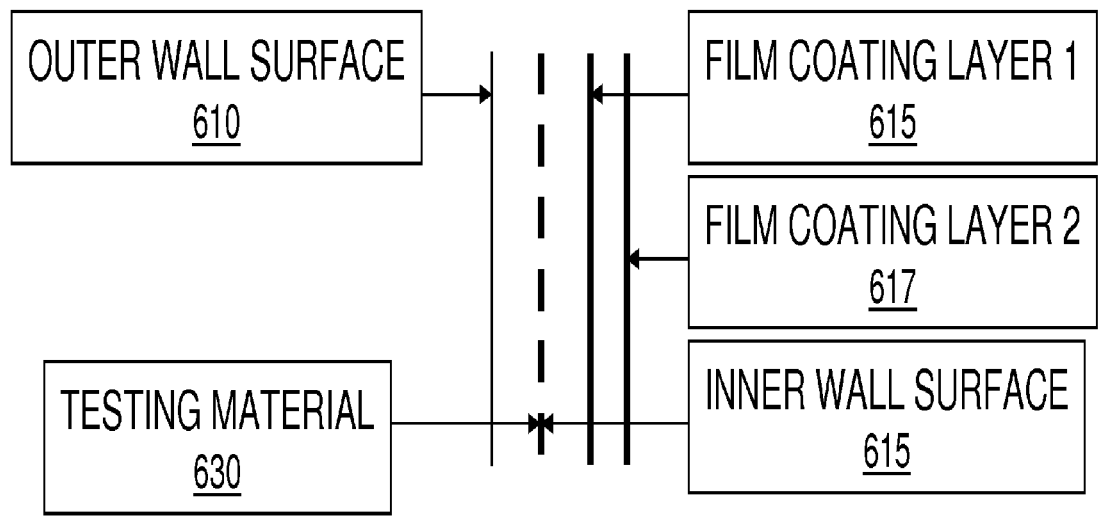
FIG. 6b is a schematic block diagram of an illustrative portion of a beverage container that may be used in accordance with the present disclosure.

In alternative embodiments, as illustrated in FIG. 6b, multiple applications (i.e., layers/coatings, 615, 617, etc.) of the same film material may be applied to a particular section to achieve the desired result of varying (e.g., slowing) the rate that the beverage in the beverage container, and therefore any drug mixed in the beverage, will pass through the film to contact the testing material. It is also contemplated that different wax types may also be applied to the same section to vary the rate. Thus, other similar methods or combinations thereof to slow or increase the rate at which the beverage in the beverage container will contact the testing material may also be used without departing from the scope and spirit of the disclosure.

Advantageously, because each section may have a known estimated time for when the beverage may pass though the film, it may be possible to discern an approximate time when a drug was placed in the beverage container. For example, assume a first section 332 of the beverage container is estimated to allow the beverage to pass though the film in about 10 minutes. Further assume that a second section 334 of the beverage container is estimated to allow the beverage to pass though the film in about 20 minutes. Further assume that once the testing material at the first section 332 is initially exposed to an uncontaminated beverage for more than, e.g., a couple minutes, then that testing material for section 332 may no longer be able to react (e.g., change color) even if subsequently exposed to a contaminate, since the reagent(s) in the testing material may be too diluted. Thus, in the example, if the first section 332 does not show a reaction, but the second section 334 does show a reaction, then it is likely that the beverage was contaminated sometime between the 10 minute period and the 20 minute period. Therefore, by comparing (i) the section which does show a reaction to (ii) the previous section that does not show a reaction, it may be possible to discern an approximate time when a drug was placed in the beverage container. This may aid in determining who drugged the beverage (i.e., who had access to the beverage within the 10 minute time span).

Figure 3C:
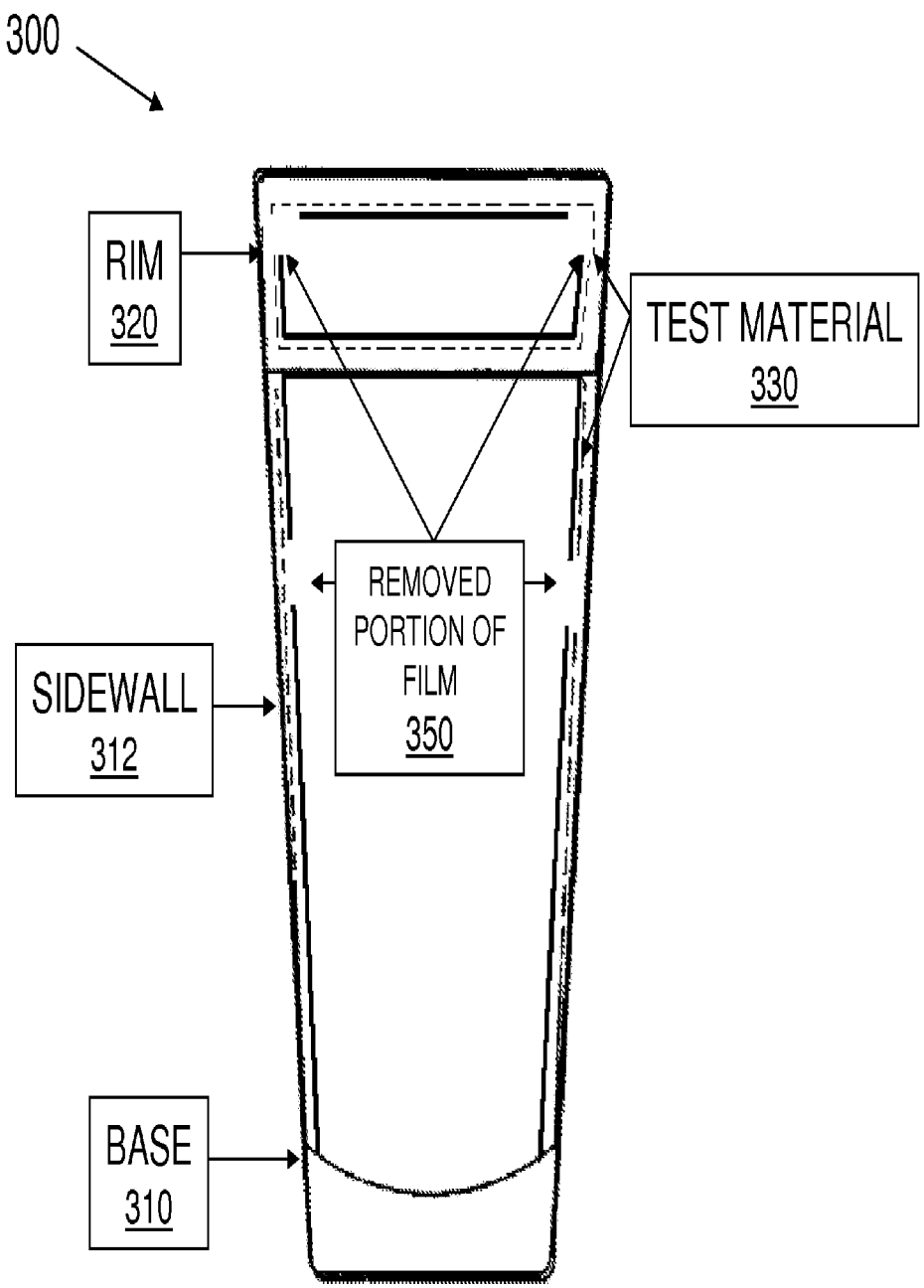
FIG. 3c is a schematic block diagram of an illustrative beverage container with a section of protective film removed that may be used in accordance with the present disclosure.

FIG. 3c is a schematic block diagram of the illustrative beverage container 300 similar to that of FIG. 3a with at least one section of protective film removed 350 that may be used in accordance with the present disclosure. In one embodiment, the user may be required to actively remove the wax lining 350 before the beverage will be exposed to the testing material. However, in an alternative embodiment, should the user desire to test the beverage for contaminants at an earlier time rather than waiting for the beverage to pass through the film 350 (as discussed with regard to FIG. 3b), the user may instead choose to, e.g., "scratch" away or otherwise remove the wax lining, thereby enabling the user to more immediately expose the beverage to the newly revealed testing material. By enabling the user to selectively remove portion(s) of the film as desired, the beverage container advantageously provides multiple locations for individual test sites and at different times. For example, the user may remove the wax lining (e.g., upper left portion) in the rim 320 at $T_1$. If the testing material shows the beverage is not contaminated, the user may continue drinking the beverage. However, if the user begins to feel strange and questions whether or not the beverage has been contaminated, the user may subsequently remove the wax lining (e.g., upper right portion) in the rim 320 at $T_2$. As noted above, using substances such as zein as the film may be beneficial as it is non-allergenic and edible. Thus, there may be no known consequence if the user were to accidentally scratch the film into the beverage and ingest it.

Advantageously, according to one embodiment, any remaining area of wax film coating the testing material may be an area capable of being used to test the beverage. That is, any area where the wax has not been removed is illustratively a viable area to test the beverage regardless of any previous tests conducted at other locations. As can be appreciated by those skilled in the art, the viability of using an area where the film has not yet been removed may depend on different factors, such as whether the beverage sampled through the removed portion of the film may "leak" to the testing material under the film that has not yet been removed. One exemplary embodiment to protect against "leaking" may be to have the testing material separated by areas of non-testing material that may be used to prevent or otherwise curtail the undesired migration of the beverage entering from the removed portion of the film. For example, sections 332 and 336 may have film covering testing material, whereas sections 334 and 338 may comprise non-testing material used as a "bumper" to prevent the beverage from crossing sections. However, allowing such cross section leaking may be beneficial for other reasons, such as an alternative way to distribute the beverage in the beverage container throughout to other portions of the testing material without further effort by the user, or as a way to maintain samples of the beverage for later use (e.g., evidence in a police investigation).

Figure 3D:
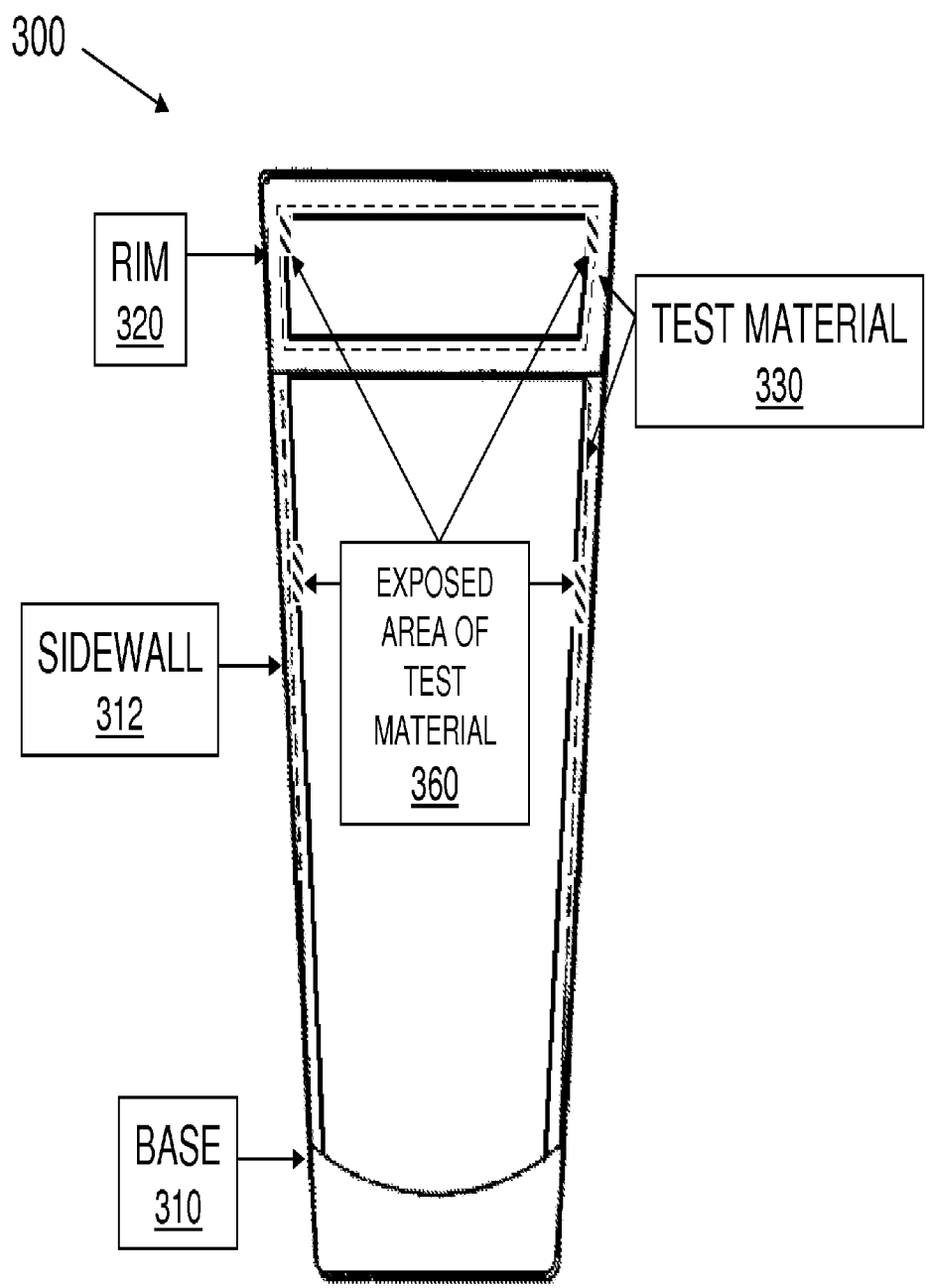
FIG. 3d is a schematic block diagram of an illustrative beverage container with a section of protective film removed that may be used in accordance with the present disclosure.

FIG. 3d is a schematic block diagram of the illustrative beverage container 300 similar to that of FIG. 3c with at least one section of protective film removed that may be used in accordance with the present disclosure. According to one embodiment, assume that the beverage in the beverage container has been contaminated with, e.g., GHB. As noted above in FIG. 3c, the section(s) of protective film have been removed 350, for example, by the user to test the beverage for contamination. As a result of removing the wax film from locations of the beverage container, those corresponding areas of testing material 330 are now exposed 360 to the beverage in the beverage container and therefore exposed to the GHB. As such, to alert the user of the contamination, the exposed area of test material 360 may display a visual alert (e.g., color change, pattern, etc.). Notably, as discussed above with regard to FIG. 3c, only the exposed area of test material 360 is affected (e.g., visually) since only those areas have the film removed, thereby exposing the testing material to the GHB in the beverage. However, the beverage may enter through any of the exposed areas to other portions of unexposed testing material, thereby providing the visual affect to those areas in addition to the exposed areas.

Figure 4:
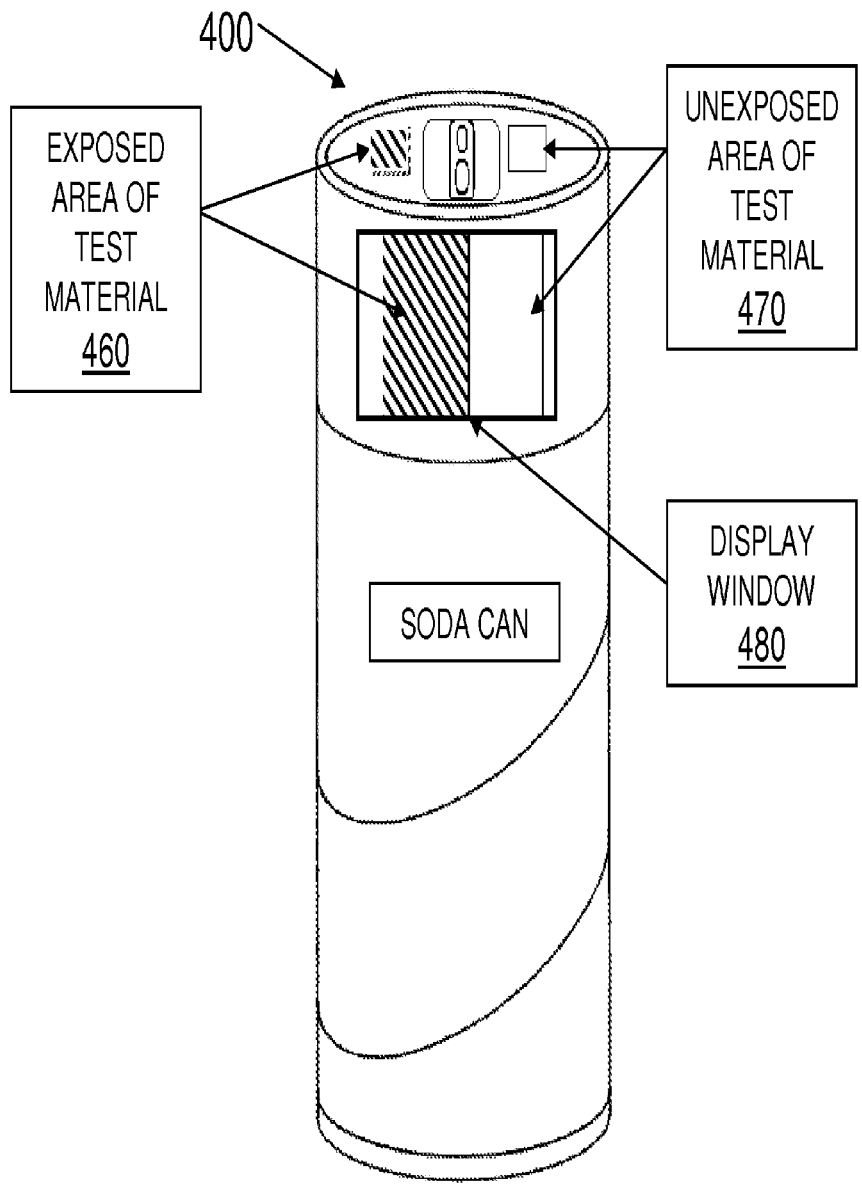
FIG. 4 is a schematic block diagram of an illustrative beverage container with a protective film that may be used in accordance with the present disclosure.

FIG. 4 is a schematic block diagram of an illustrative beverage container 400 with a protective film that may be used in accordance with the present disclosure. According to one embodiment, the beverage container may be a can (e.g., aluminum can) such as the kind typically used to hold soda, beer, and other beverages. The beverage container illustratively comprises drug testing material in various locations. For example, the testing material (e.g., exposed/unexposed 460/470 respectively) may be directly affixed to the top of the beverage container, or alternatively, on the outer sidewall. Some of the beverage may tend to pool on that surface as a result of the motions involved while drinking from the beverage container. Thus, it may be less cumbersome for the user to test the beverage by using the portions of the beverage already pooled on the top, for example, in an embodiment where the beverage container is a closed top beverage container.

According to another illustrative embodiment, assume that the beverage in the beverage container 400 has been contaminated with, e.g., Rohypnol. Similarly to FIG. 3c, some section(s) of protective film have been removed (i.e., exposed area of test material 460), for example, by the user to test the bever- age held by the beverage container. On the other hand, some section(s) of protective film have not yet been removed (i.e., unexposed area of test material 470). As a result of removing the wax film from these locations of the beverage container, those corresponding areas 460 of testing material are now capable of being exposed to the beverage and therefore exposed to the Rohypnol. As such, to alert the user of the contamination, the exposed area of test material 460 displays a visual alert (e.g., color change, striped or other pattern, etc.). Notably, according to the embodiment, any remaining area of wax film coating the testing material (i.e., unexposed area of test material 470) may still be an area capable of being used to test the beverage at a subsequent time (e.g., depending on how porous the film coating the unexposed area is).

According to another embodiment, a portion of the beverage container 400 may be removed and then replaced with the testing material. In the embodiment, it may be beneficial to apply another coating of a liquid resistant wax on the outer most side of the testing material to prevent dripping. In the illustrative embodiment, the testing material may be part of the inside of the beverage container, where any indication of contamination from the testing material may be viewed through a display window 480. Preferably, the display window 480 should be of a sufficiently transparent or translucent material, e.g., plastic or otherwise, that allows a user to sufficiently discern a change in the testing material caused by beverage contamination within the beverage container. This may be advantageous in embodiments such as those where inside of the beverage container comprising the testing material is not otherwise viewable by the user (e.g., closed top beverage containers). Alternatively, the display window may be configured such that when no contamination is detected in the beverage contained within the beverage container, the display window is disguised as, for example, a logo of the beverage container.

Figure 5A:
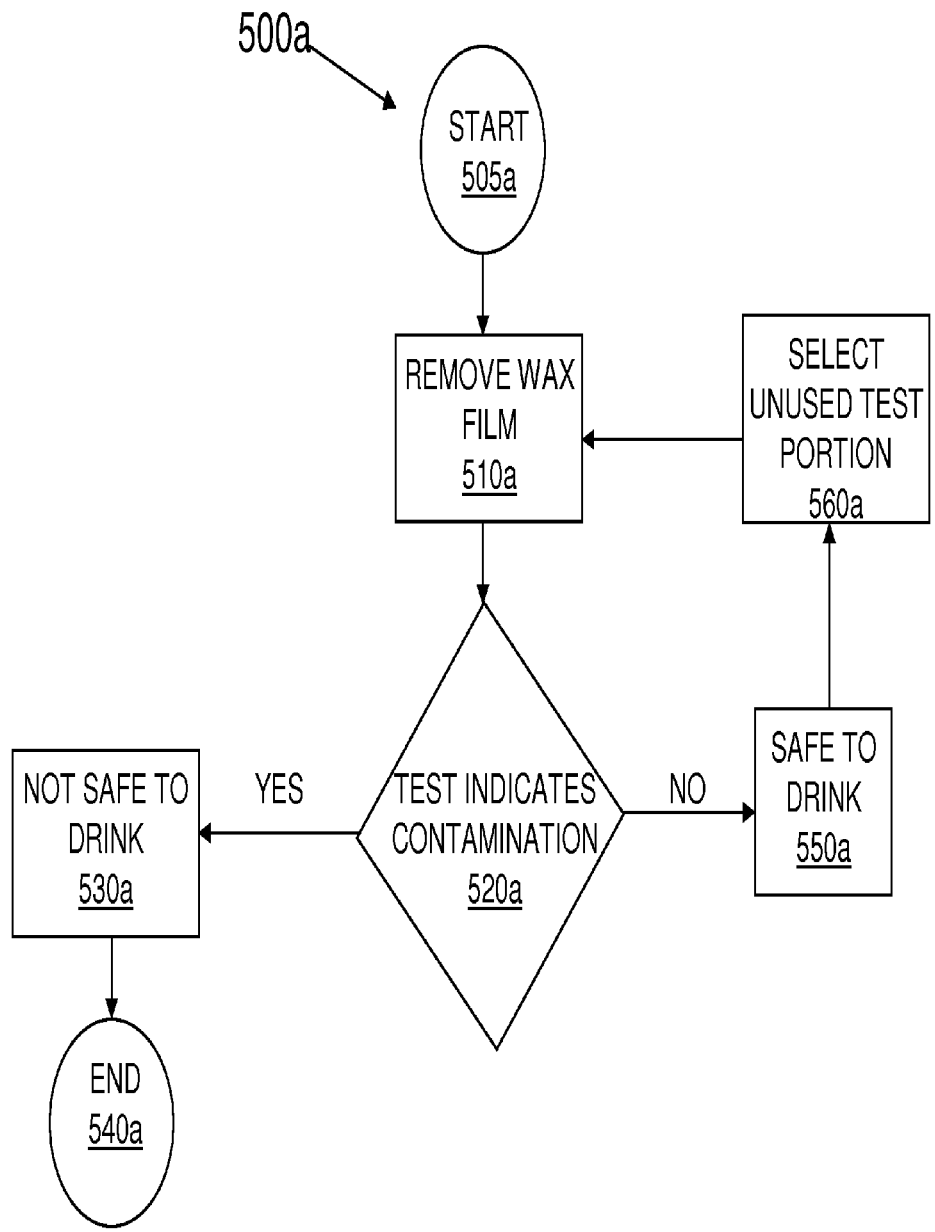
FIG. 5a is an illustrative procedure for using the beverage container in accordance with one or more embodiments of the present disclosure.

FIG. 5a is an illustrative procedure for using the beverage container in accordance with the present disclosure described herein where the (e.g., wax) film is readily removable by the user. This illustrative procedure assumes a beverage is currently contained within the beverage container. The procedure 500a starts at step 505a, and continues to step 510a, where at least a portion of the wax film is removed, e.g., by the user. As noted above, the wax film prevents the beverage contained within the beverage container from immediately contacting and reacting with the testing material lined, for example, within the inner surface of the sidewall 312, the base 310, the rim 320, or the top (e.g., as similarly shown by example in either FIG. 3a-d and/or FIG. 4 above). Thus, should the user desire to test the beverage for contaminants, the user need only, e.g., "scratch" away or otherwise remove the wax lining, thereby exposing the beverage to the newly revealed testing material. In alternative embodiments, as noted above, the scratching step is not necessarily required, since the beverage may be automatically tested according to, e.g., how porous the (wax) film is. Notably, in embodiments where no such film is present, step 510a and 560a may be skipped. Once the testing material is exposed to the beverage, it is determined whether the testing material indicates that the beverage is contaminated (e.g., with a drug) in step 520a. If yes, the procedure moves to step 530a where the testing material indicates that the beverage is not safe to drink Any type of indication or alert is contemplated where the user is made aware of the outcome of the test. For example, the indication may be visual (e.g., a color change in the test material). However, any suitable means of indication may be used. The procedure then ends at step 540a.

However, if at step 520a the determination is no, the procedure moves to step 550a where the testing material indicates that the beverage is safe to drink Such an indication, if any, may be the absence of a visual indicator. However, any suitable indication (e.g., visual or otherwise) may be used. The beverage container may comprise multiple locations for individual testing by scratching away the wax film from different locations as desired. This may be useful in such situations where the user is unsure about the accuracy of the previous test and would like to re-test the beverage using another location. This may also be useful, for example, where a beverage has tested negative for contamination at time $T_1$, but the user believes that the beverage may have been subsequently contaminated at time $T_2$. The procedure then moves to step 560a where the user may select an unused test material portion for another test. The procedure then loops back to step 510a.

Figure 5B:
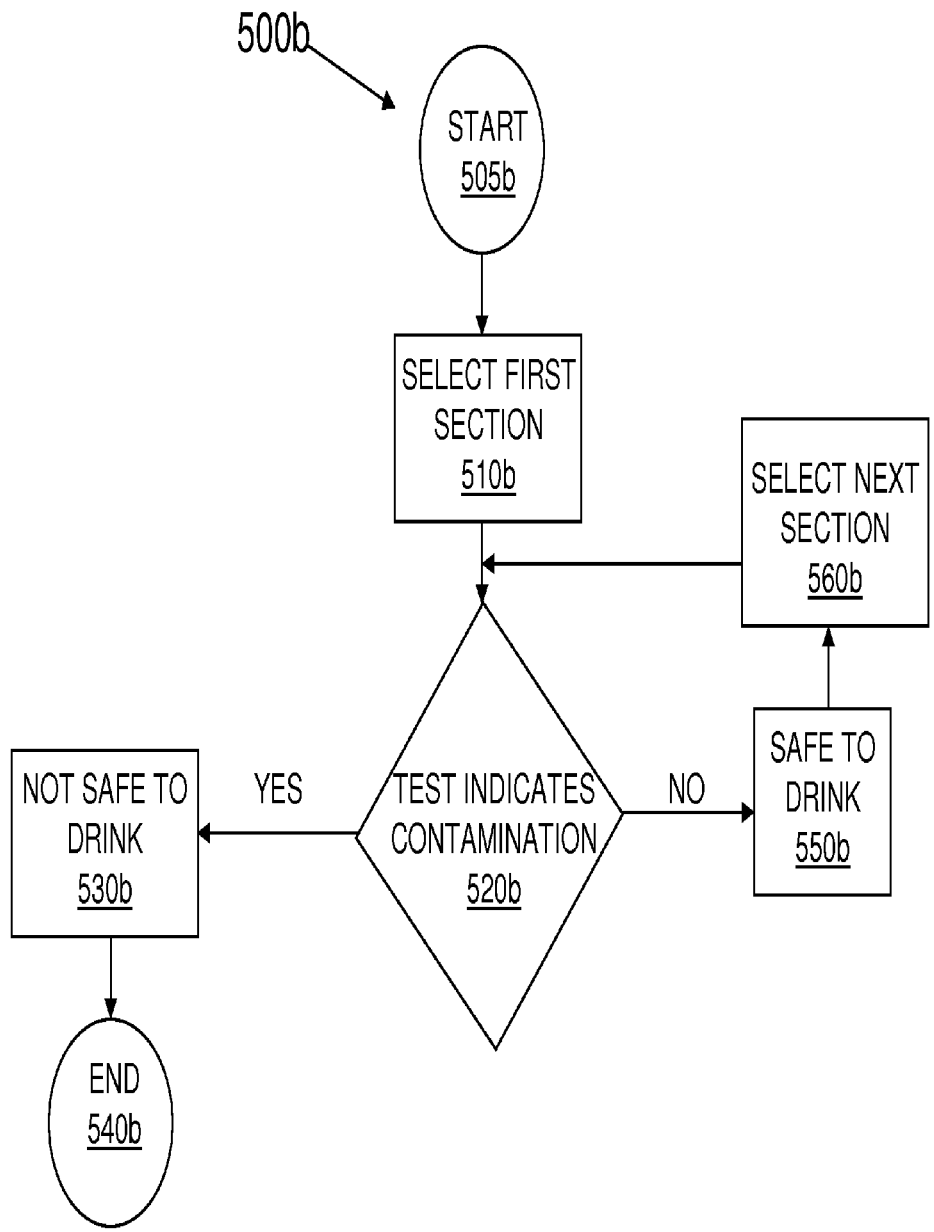
FIG. 5b is an illustrative procedure for using the beverage container in accordance with one or more embodiments of the present disclosure.

FIG. 5b is an illustrative procedure for using the beverage container in accordance with the present disclosure where at least a portion of the (e.g., wax) film is not required to be removed by the user. FIG. 3b is an example embodiment which may apply to the procedure. This illustrative procedure assumes a beverage is currently contained within the beverage container. The procedure 500b starts at step 505b, and continues to step 510b, where a first section of the beverage container 332 is selected to check for a visual indication of contamination of the beverage within the beverage container. As noted above, the film prevents the beverage contained within the beverage container from (immediately) contacting and reacting with the testing material lined, for example, within the inner or outer surface of the base 310, the rim 320, the sidewall 312, or the top (e.g., as similarly shown by example in either FIG. 3a-d and/or FIG. 4 above). Thus, should the user desire to test the beverage for contaminants, the user need only, e.g., "scratch" away or otherwise remove the wax lining, thereby exposing the beverage to the newly revealed testing material. However, this scratching step is not necessarily required in order to test the beverage due to the porous nature of the film as described above. For example, as discussed above, each section may allow for varying times when the beverage may pass through the film to the testing material, e.g., depending on the porous nature, type, and/or amount of the film used at each section. Once the testing material of the first section of the beverage container is exposed to the beverage, e.g., either by removing the film or due to the porous nature of the film, it is determined at $T_1$ whether the beverage container at the first section indicates that the beverage is contaminated with a drug in step 520b. If yes, the procedure moves to step 530b where the beverage container indicates that the beverage is not safe to drink Any type of indication or alert is contemplated where the user is made aware of the outcome of the test. For example, the indication may be visual (e.g., a color change in the test material). However, any suitable indication technique may be used. The procedure then ends at step 540b.

However, if at step 520b the determination is no, the procedure moves to step 550b where the beverage container at section one indicates that the beverage is safe to drink. Such an indication may be the absence of a visual indicator. For example, if the beverage container is white by default, and if the visual indicator is a color change, then the beverage container remaining the default color (i.e., white) may be considered an absence of a visual indicator. However, any suitable indication method or technique may also be used. The procedure then moves to step 560b where the user may wait and select/view the next section to check for a visual indication showing whether the beverage is now contaminated at $T_2$. Notably, as discussed above, the next section of the beverage container may automatically re-test the beverage, or allow the user to remove the film to more immediately expose the beverage to the testing material. The procedure then loops back to step 520b.

In a preferred embodiment, the beverage container is the testing material and vice versa (e.g., replacing a portion of the beverage container with the testing material, directly attaching the testing material to a portion of the beverage container, etc. as illustratively discussed with regard to FIG. 1 and FIG. 3a), as opposed to prior testing devices/kits like the one described in the above mentioned U.S. patent application Ser. No. 11/899,646, titled STRAW HOLDER INTEGRATED WITH A BEVERAGE CONTAINER, where the testing material is part of an entirely separate component, and where the separate component must then be connected to the beverage container. As such, the user illustratively is not required to remember to bring a test kit component or to use the test kit. However, in alternative embodiments, the testing material may also be provided separately from the beverage container (e.g., with or without the wax lining applied to the testing material) to be affixed or bonded to the beverage container at a later time (e.g., using an adhesive or other suitable material). For example, one side of the testing material may comprise the adhesive, while the other side may comprise the wax lining. In the embodiment, it may be advantageous to have the adhesive be resistant to liquid so as to prevent the beverage from circumventing the wax film to the testing material. Providing the testing material separately may be useful, inter alia, for example, where the beverage container (e.g., beer glass, porcelain coffee mug, etc.) is not conventionally disposable as is, e.g., a paper cup. For instance, a public bar using their own glasses to serve alcohol may benefit from an embodiment where the separate replaceable testing material lines the glasses instead of requiring the bar owner to acquire the disposable beverage containers, where the testing material is "built-into" the beverage container. That is, a used testing material in the non-disposable beverage containers may be replaced with a new testing material.

Figure 7:
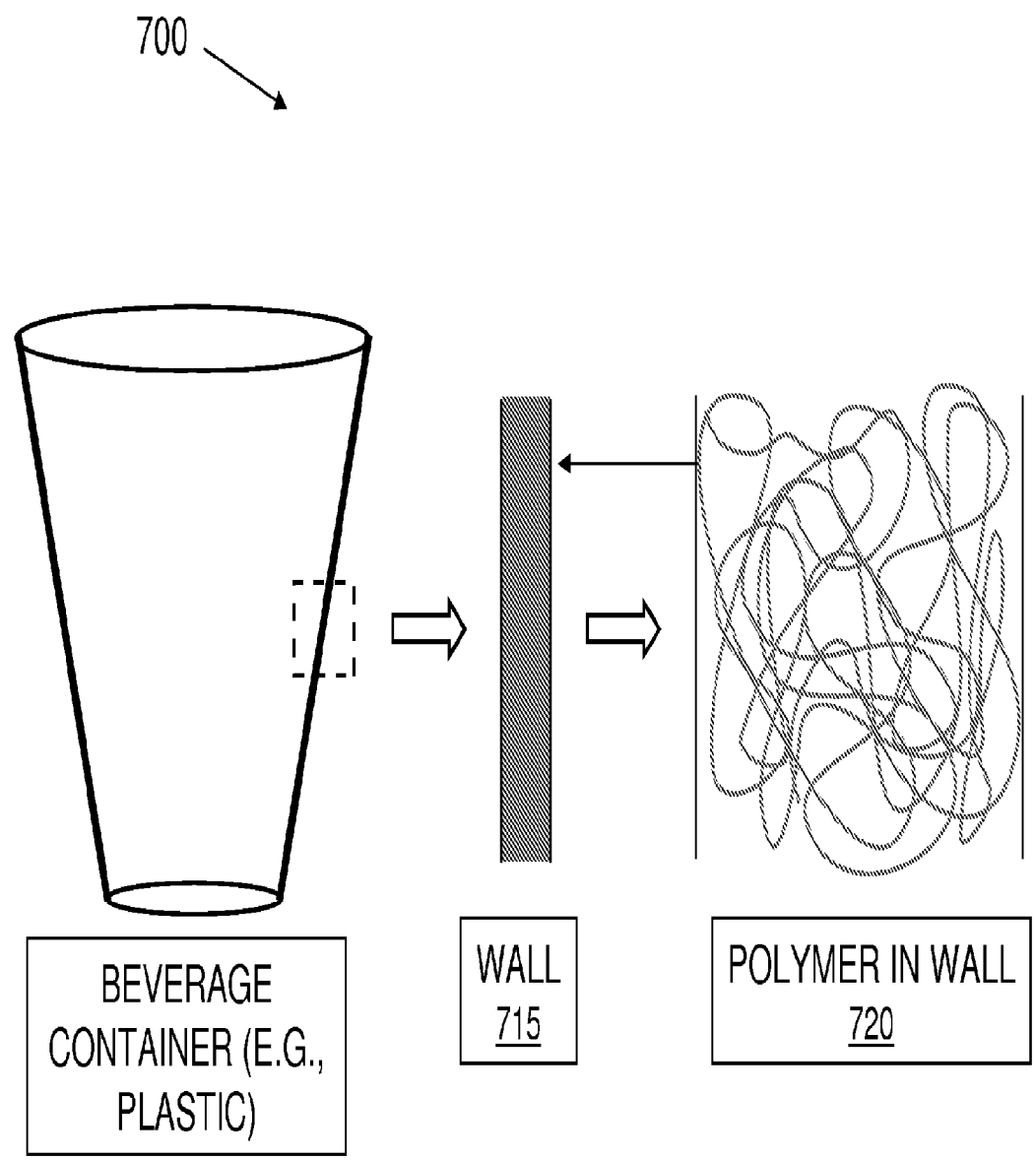
FIG. 7 is a schematic block diagram of an illustrative beverage container that may be used in accordance with one or more embodiments of the disclosure.

FIG. 7 is a schematic block diagram of an illustrative beverage container 700 that may be used in accordance with one or more embodiments of the present disclosure. An indicator (e.g., recognition site for one or more substances) may be combined (i.e., incorporated) onto a polymer from which the beverage container is made. Illustratively, this may be accomplished, e.g., by direct modification of the polymer 720 from which the plastic (and/or other material) in the beverage container (e.g., wall surface 715) is made. While FIG. 7 is described in terms of the polymer in a specific portion of the beverage container, i.e., wall surface 715, any or all portions of the beverage container may also be used (including within wall 715). As such, the description of using any specific portion of the beverage container should be taken as exemplary only. A polymer, as is known to those skilled in the art, is broadly described as a linear (although it need not be linear) molecule comprising repeating structural "units" (i.e., monomers). For example, polyvinyl chloride, or PVC (e.g., white plastic typically used to make pipes for cold water return in homes), may be described as a polymer comprising repeating units of vinyl chloride monomers that are linked, e.g., serially via chemical bonds to form a long, "spaghetti-like" molecule. A polymer generally may contain pendant chemical groups on each repeat unit at which an indicator may be incorporated. Illustratively, according to one or more embodiments, the indicator may be pre-attached to the monomer prior to polymerization and/or post-attached after the polymer has been made.

Although FIG. 7 illustrates "linear" polymers typically used in industry, those skilled in the art will appreciate that linear polymers also can be cross-linked to form two-dimensional and three-dimensional polymers. As such, any particular description of a "linear" polymer or otherwise should be taken as exemplary only and not to otherwise limit the scope of the disclosure. Cross-linking is a technique known to those skilled in the art, for example, to make plastics derived from polymers stronger and less flexible. Cross-linking may illustratively be accomplished by incorporating monomers that have pendant chemical groups that are reactive such that the pendant chemical groups on different sections of the linear polymer chain react with one another on contact to form a chemical bond. Cross-linking of the linear polymer chains in that manner results in a two-dimensional or three-dimensional polymer. Cross-linking requires that at least some of the pendant chemical groups on the linear polymer are reactive such that they cross-link the polymer chains. That can be accomplished using different methods known to those skilled in the art.

For example, a first illustrative method is to prepare the polymer using a mixture of at least two different monomers, one of which may contain the indicator or a reactive chemical group that will bind to the indicator, the other of which contains a reactive chemical group that is capable of cross-linking the polymer chains by forming a chemical bond. That concept may be illustrated in FIG. 10 described further below for a block co-polymer. In that example, the sections 1015A of polymer are generated from monomers containing the indicator as a pendant group. Incorporating reactive pendant groups into the sections 1015B of polymer would result in a cross-linked polymer. In this illustrative embodiment, some of the monomers contain the indicator, and some contain the cross-linking groups. The first illustrative method may differ, for example, from that described in another illustrative method described below, in which the monomers contain both the indicator and a reactive chemical group capable of cross-linking. While some specific examples of accomplishing cross-linking are illustratively described, those skilled in the art will appreciate that other cross-linking methods may also be used. As such, any particular cross-linking example should be taken as exemplary only and not to limit the scope of the disclosure. For example, cross-linking may be accomplished using block co-polymers where the monomers containing the indicator and those containing the cross-linking groups are segregated. Cross-linking also may be achieved by simply mixing the different monomers such that the resulting polymer chain contains a random, disordered arrangement of the different monomers instead of segregated sections of like monomers. Cross-linking by forming a chemical bond between pendant reactive chemical groups may be accomplished by having the pendant chemical groups react with one another via chemical reactions that differ from those used to link the monomers into polymers. As can be appreciated by those skilled in the art, there are many commonly known reactive groups for this. Cross-linking reactions also generally require two different reactive chemical groups for a reaction to occur between the two groups. Generally, according to one or more illustrative embodiments, one type of reactive chemical group is not reactive with itself. There are known examples where chemical groups do react with themselves, and are contemplated with one or more illustrative embodiments.

Another illustrative method is to prepare a polymer using at least two different monomers, one of which features a pendant group comprising both the indicator and also a reactive chemical group capable of cross-linking, and the other of which comprises the indicator and a chemical group capable of cross-linking. In this illustrative method, the monomers contain both the indicator and the reactive cross-linking group in the same pendant group. This concept may be illustrated in FIG. 8 where 805 is the indicator/recognition site, and 810 is the linker illustratively comprising the cross-linking group. Both illustrative (or other known) methods may result in formation of a linear polymer containing the indicator than can undergo cross-linking via reaction of the cross-linking groups to form a two-dimensional or three-dimensional cross-linked polymer.

Figure 8:
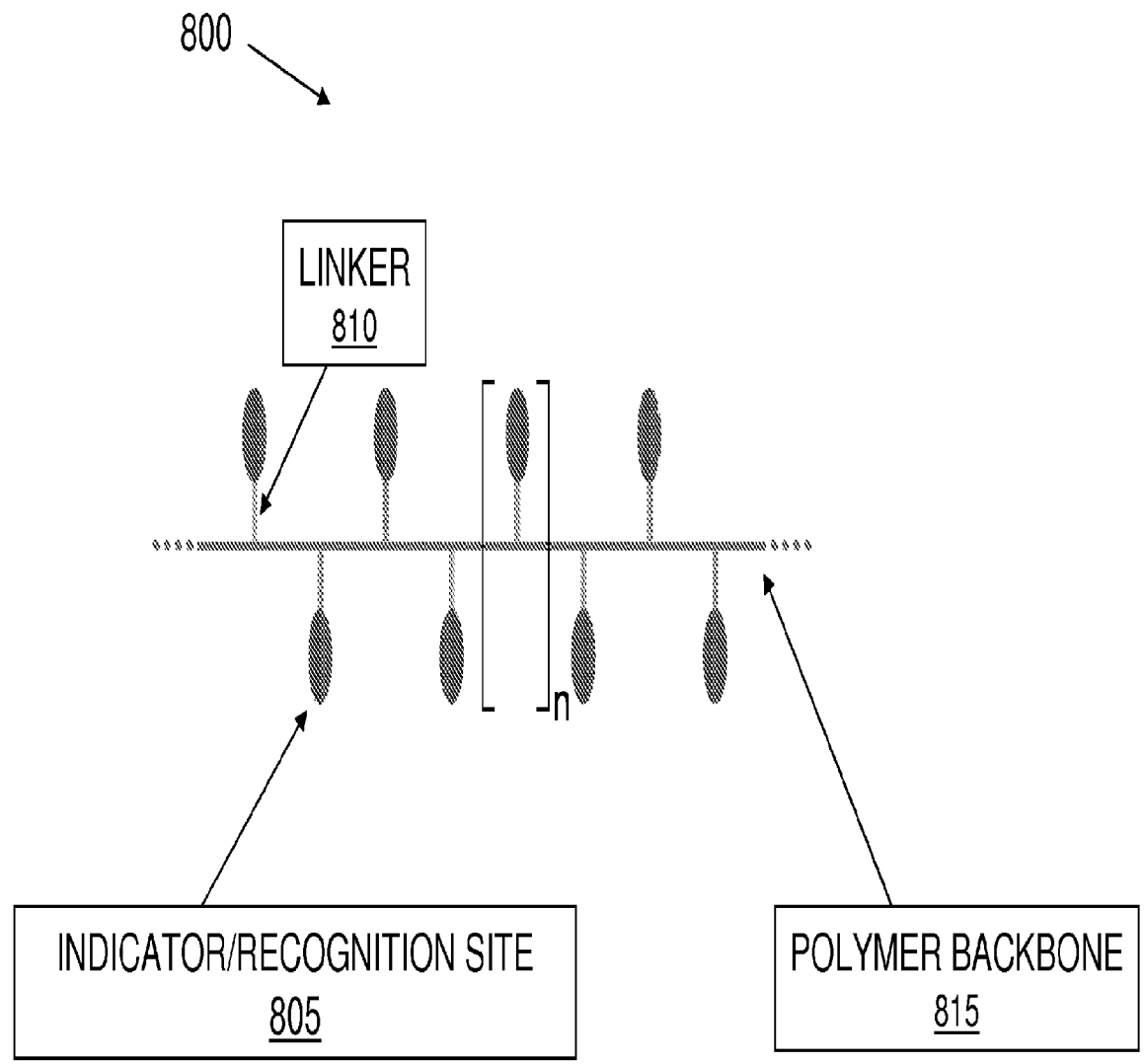
FIG. 8 is a schematic block diagram of an illustrative material of a beverage container that may be used in accordance with one or more embodiments of the disclosure.

According to one or more illustrative embodiments, such as the one shown in FIG. 8, indicator 805 may be attached (e.g., combined) onto a backbone 815 of a polymer 800 (e.g., a pure polymer) of a beverage container via linker 810. One or more indicators 805 exposed on the surface of the beverage container may be available to react with any specific drug (or other specific substance) that comes into contact with the surface (indicators). The repeat unit (i.e., the monomer starting material that may be used to make the polymer) is indicated in brackets, where n indicates the number of repeat units in the polymer.

Figure 9:
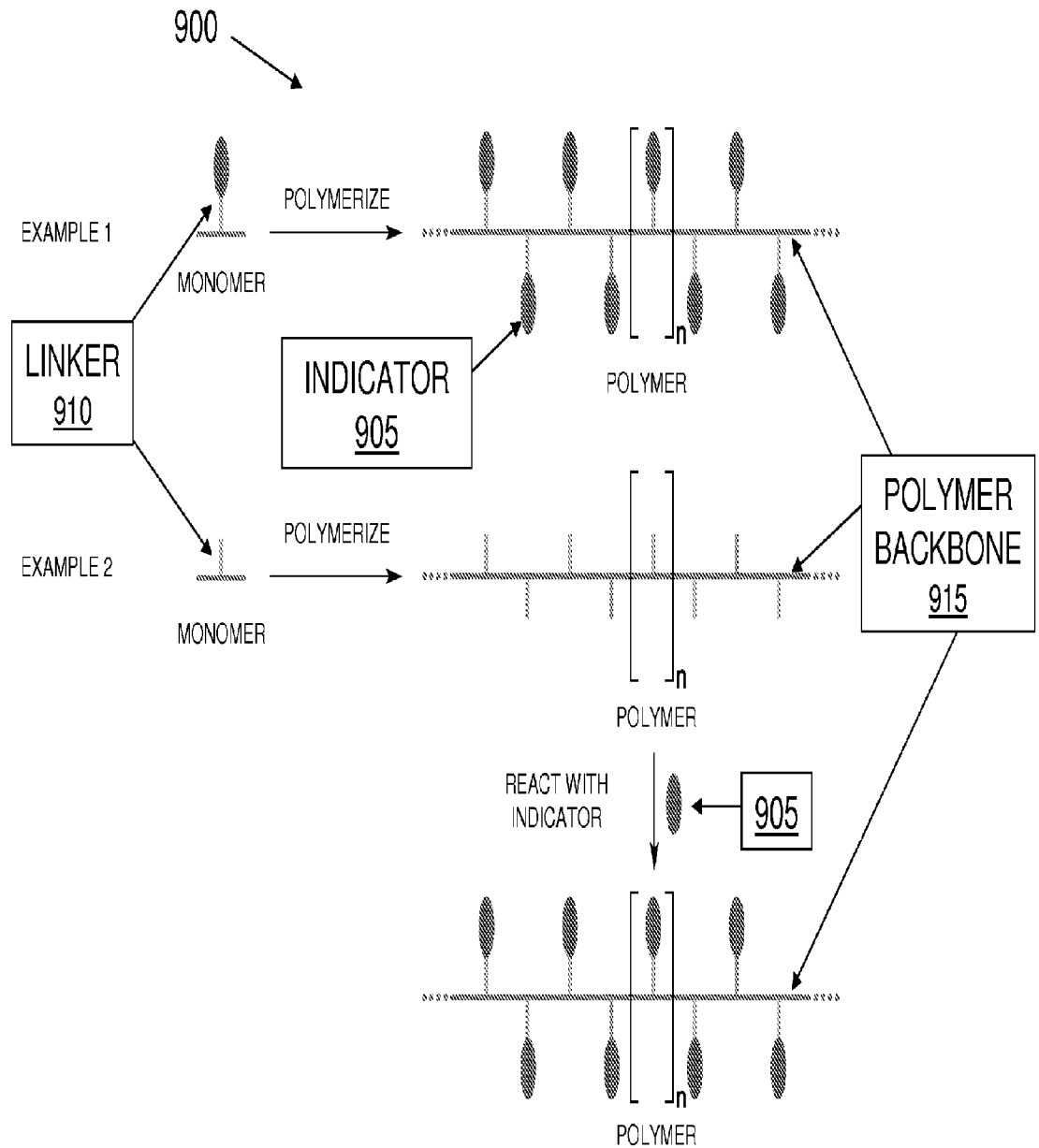
FIG. 9 is a schematic block diagram showing exemplary techniques/procedures for preparing one or more materials with attached indicators that may be used in accordance with one or more embodiments of the disclosure.

FIG. 9 is a schematic block diagram showing exemplary techniques/procedures 900 for preparing polymers of a beverage container with attached (e.g., combined) indicators 905 that may be used according to one or more embodiments of the disclosure. Illustrative example 1, according to one or more embodiments, comprises using a monomer (e.g., the starting material used as the repeat unit in the backbone of the polymer) that may contain a selected indicator bound to the monomer via a chemical bond (i.e., pre-attachment). As alluded to throughout, the appropriate indicator(s) may be selected depending on, e.g., the specific/particular substance(s) that is to be detected. The chemical bond may consist of any type of chemical bonding interaction such as a covalent bond (a normal chemical bond between two atoms (e.g., that are not metals)), an ionic bond (a bond between positively and negatively charged ions), or a weaker intermolecular bond/force (e.g., hydrogen bond, dipole-dipole bond, ion-dipole bond, van der Waals bond, etc.) that results in attachment of the indicator to the monomer. Those skilled in the art will appreciate that any other pre-attachment techniques may also be used that results in attachment of the indicator to the monomer. As such, any particularly disclosed pre-attachment technique should be taken as exemplary only and not to limit the scope of the disclosure. Formation of the corresponding polymer via polymerization of the monomer (e.g., a chemical reaction between the monomers that links them together) may create a plastic (and/or other material) with surface-exposed indicators. Forming polymers via a chemical reaction between monomers (e.g., radical polymerization, cationic polymerization, anionic polymerization, or other types of polymerization reactions, etc.) is well-known in the art.

Illustrative example 2, according to one or more embodiments, comprises using a monomer with a reactive linking group to which the indicator can be attached after the polymer is prepared (i.e., post-attachment). Post-attachment of the indicator to the reactive linking groups on the backbone 915 of the polymer may be achieved, for example, by reacting/exposing the polymer to indicator 905. For attachment to occur, the indicator should preferably contain a reactive group that will form a chemical bond with the reactive linking groups. The chemical bond may consist of any type of chemical bonding interaction such as a covalent bond (a normal chemical bond between two atoms (e.g., that are not metals)), an ionic bond (a bond between positively and negatively charged ions), or a weaker intermolecular bond/force (e.g., hydrogen bond, dipole-dipole bond, ion-dipole bond, van der Waals bond, etc.) that results in attachment of the indicator to the polymer (e.g., of the beverage container). Those skilled in the art will appreciate that any other post-attachment techniques may also be used. As such, any particularly disclosed post-attachment technique should be taken as exemplary only and not to limit the scope of the disclosure. Notably, example 2 (e.g., attaching an indicator to the polymer/plastic after the beverage container has been manufactured) offers a potential advantage of requiring less of the indicator, e.g., since attachment of the indicator will (mostly, if not entirely) occur only on the surface of the beverage container, rather than within the interior of plastic/polymer. Those skilled in the art will appreciate that attachment (e.g., post-attachment) of the indicator may occur at different phases of the manufacturing process (i.e., any time between the beginning and end of manufacturing of any portion of the beverage container that may eventually be used to create a beverage container of the present disclosure. For example, according to one or more illustrative embodiments, post-attachment during the manufacturing process time to the finished plastic container (e.g., after the polymer/plastic is processed to form a beverage container) may result in attachment of the indicator on the surface of the beverage container. However, some indicator also may diffuse into the finished plastic and become attached within the interior of the plastic as well as on the surface. According to one or more alternative embodiments, attachment (e.g., post-attachment) of the indicator may be carried out during the manufacturing process time after the polymer is prepared but before the polymer is processed to form, e.g., a beverage container. Post-attachment to the polymer (not the finished plastic) may illustratively result in attachment of the indicator at all or most of the linker sites. In that case, the indicator may be present both at the surface and within the plastic when it is prepared from the polymer comprising the post-attached indicator.

Both examples, whether carried out before and/or during and/or after the beverage container has been manufactured/created, result in a polymer (e.g., when a polymer is illustratively used) with attached indicators exposed at least at the surface (and/or according to one or more embodiments, within the interior of the plastic). Those skilled in the art will appreciate that, in any illustrative embodiment throughout where appropriate, the indicator may be applied/attached/combined, incorporated, etc. to any portion of the surface of (and/or within) the beverage container and may be done using any technique that brings the indicator into contact with the plastic/polymer (or other usable material) such that the indicator is enabled to react to form a chemical bond (e.g., via spraying, dipping, rolling, stamping, printing, evaporating, etc.). Moreover, other differing techniques are also contemplated. Thus, any description of any particular indicator "attaching" (e.g., combining/incorporating, etc.) technique described throughout, or otherwise (or combination thereof) should be taken as exemplary only and not to limit the scope of the disclosure.

Similarly to the illustrative description of, e.g., FIG. 2 above, such techniques may allow application of the indicator onto defined regions/sections of the beverage container to enable different (or identical) indicators to be patterned on its surface. According to one or more illustrative embodiments, testing material of the beverage container may be made using either example for multiple drugs rather than a single drug, e.g., by incorporating a "cocktail" mixture of different indicators into or onto the surface of the polymer/plastic via pre-attachment and/or post-attachment and/or by patterning different indicators in different and/or same locations on the surface of the polymer/plastic. Those skilled in the art will appreciate that the material of the beverage container may be made to test/monitor for a single drug or multiple drugs. As used throughout, unless otherwise suggested, the term indicator may be used to denote one or more indicators.

Notably, the ability of the human eye to detect a colorimetric response (i.e., change in color) of the beverage container (i.e., via a colorimetric response of the indicator) may depend on multiple factors. For example: the amount (i.e., concentration) of the drug in the beverage, the amount (i.e., concentration) of the indicator(s) present on or in the material of the beverage container, the amount of the drug that binds to the indicator(s), the sensitivity of the indicator to the drug and the corresponding response of the indicator (e.g., ability to cause a dramatic "detectible" color change). As such, if the response "detected" on the chemical level but not sufficiently so that it may be detected by the human eye, or if the response is detected by the human eye but the response is desired to be more prominent, more indicators may be added onto or within the material of the beverage container and/or the thickness of the coating with the indicator(s) may be increased. Advantageously, taking at least the above factors into consideration, the present disclosure makes it is possible to vary the concentration of the indicator, not only to detect nearly any relevant drug concentration (i.e., a concentration resulting in a noticeable effect to whomever consumes the drug), but also as a tool to measure when at least a minimum concentration of a substance is reached. As an example, the beverage container may be used to detect whether or not a city water supply contains too much, e.g., fluoride or other substance (i.e., when a concentration threshold has been met), or if a maximum dosage of a medication has been reached, etc.

According to one or more alternative embodiments that may help a visual reaction be more detectible to the human eye, the beverage container may be made to fluoresce in response to detecting a drug in the beverage. This may be particularly advantageous in situations where the surrounding environment is dark or where a UV light source (e.g., black light or similar 254 nanometer or other UV wavelength light) may readily be available (e.g., night club, fraternity party, etc.). As can be appreciated by those skilled in the art, a fluorescent response may depend on the indicator, the materials used to anchor the indicator to the beverage container, and possibly the contents of the beverage. The concept of using a fluorescent indicator may not differ in implementation from other embodiments described throughout, in that, generally, e.g., a different type of indicator (i.e., fluorescent) is used instead. One potentially functional difference may be that fluorescent indicators may not be specific for a particular compound (i.e., a drug) the way, say, Zimmerman's Test Reagents are selected for detection of diazepam (i.e., that reagent is specific for that class of compounds). Fluorescent indicators, however, tend to react with any UV absorbing compound. Thus, the use of fluorescent indicators may produce higher amounts of false positives. With that being said, the use of fluorescents may be used as a means of making indicators that are selected specifically for a particular compound be more visible on the surface of the beverage container, rather than being used as the drug/substance indicator itself (i.e., as a contrasting background for the selected drug indicators).

An illustrative technique that may be used to implement the fluorescent embodiment(s) is called Thin Layer Chromatography (TLC), which is well known in the art, used to create a TLC plate. The concept of TLC may be applied to the material of the beverage container. That is, the material in the wall of the beverage container may contain an absorbent material (e.g., paper, plastic, silica gel, alumina, zeolite, or other porous/absorbent material, etc.) with an embedded and/or attached (chemically bonded) fluorescent indicator. Alternatively, the material in the wall of the beverage container may contain an embedded and/or attached (chemically bonded) fluorescent indicator on the surface in the absence of an absorbent material. In addition, the material in the wall of the beverage container preferably has a light color so that a change in color under a UV lamp may be seen better with the human eye. Advantageously, TLC plates are generally white.

Compounds on the TLC plate may also be visualized on the TLC plate in other ways. For example, if the compound is highly colored, it may appear as a colored spot all on its own without using a UV lamp. As another example, compounds on a TLC plate may also be visualized by exposing the plate to a chemical reagent that reacts with the compound on the plate, causing a color change. However, the latter an approach may not be the most preferable since the walls of the beverage container may need to be sprayed with a chemical reagent, which may bring up safety issues. Those skilled in the art will appreciate that any method of using fluorescents (and/or any other techniques to create a better contrasting background) with the beverage container may be used without departing from the scope of the disclosure.

According to one or more illustrative embodiments, a "drop" of a solution containing a compound or mixture of compounds may be placed onto the surface of a thin layer (e.g., less than 1 mm) of fine silica gel (glass) particles that are bonded to plastic or glass-backed plate. The TLC plate may then be placed, e.g., vertically, into a beaker containing an organic solvent. On contact with the TLC plate, the solvent may wick up the TLC plate in a manner similar to water wicking up a paper towel. Illustratively, as the solvent moves up the plate, it interacts with the compounds spotted on the silica gel, pulling them up the plate. The compounds are attracted to the silica gel and to the solvent as it moves by. As the compounds are dragged along the plate by the solvent, they may move at different rates, causing them to separate based on differences in their polarity. Once the solvent moves most of the way up the plate, the plate is removed from the solvent and dried. UV light may then be used to visualize (see) the separated compounds. A 254 nanometer ((nm) wavelength light) UV lamp is held over the TLC plate, where the compounds appear as colored spots on the plate.

Figure 10:
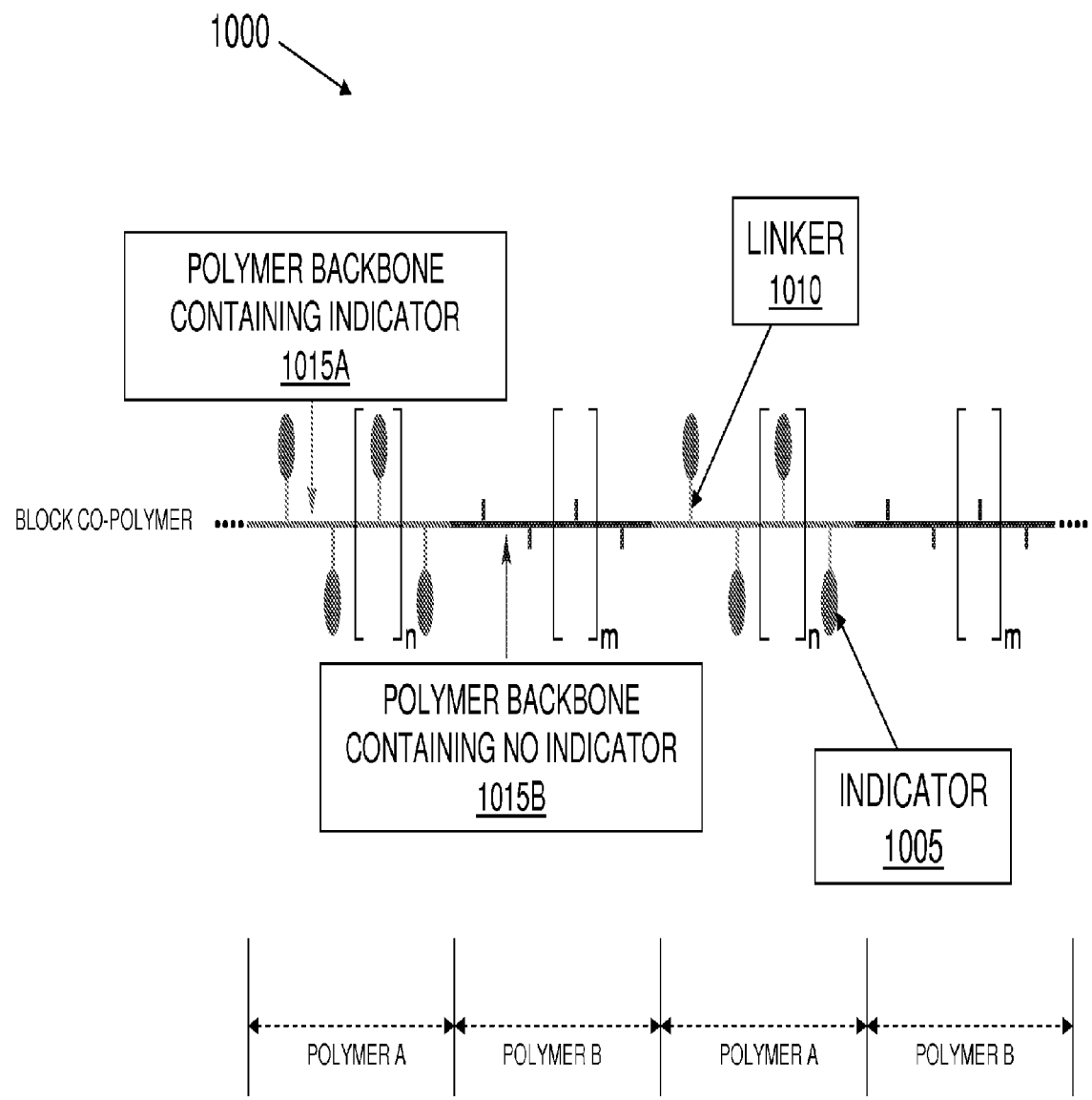
FIG. 10 is a schematic block diagram of an illustrative beverage container that may be used in accordance with one or more embodiments of the disclosure.

While one or more illustrative embodiments are described in terms of a (pure) polymer, it is contemplated that a co-polymer (or cross-linked co-polymer noted above) may also be used. FIG. 10 is a schematic block diagram of a co-polymer 1000 of a beverage container that may be used with one or more embodiments of the disclosure. Repeat units of the different polymer segments are indicated in brackets, where n and m indicate the number of repeat units in each segment. A co-polymer differs from a pure polymer, e.g., in that it may feature alternating segments of two or more different polymers (e.g., polymer A and polymer B). Therefore, some or all of the disclosure applied to the pure polymer may also be applied to a co-polymer. For instance, similarly to the description of FIG. 8, indicator 1005 may be attached (e.g., secured, affixed, combined, incorporated, etc.) onto the backbone of a co-polymer (e.g., 1015A of polymer A) via linker 1010, and similar to the above disclosure of FIG. 9, indicator 1005 may be introduced on the polymer either via pre-attachment and/or post-attachment. Moreover, testing for multiple drugs rather than a single drug can be carried out by incorporating a "cocktail" mixture of different indicators into the plastic/co-polymer, e.g., by incorporating a range of different indicators into different and/or same segments and/or as mixtures within the same segment of the co-polymer.

The properties of the different segments, such as the lengths, may be varied to control the material properties of the corresponding plastic/polymer. For example, if polymer B segments impart specific desirable properties to the polymer (e.g., strength, handling of the material, etc.), then the relative amount of the polymer B segments may be increased (or decreased) while still allowing attachment of indicator 1005 on the polymer A segments. While polymer backbone 1015B is described without an indicator, this need not be a requirement. For example, those skilled in the art will appreciate that other indicators (e.g., fluorescent) may still be attached, or alternatively as noted above, reactive chemical cross-linking groups may illustratively be attached to create a stronger plastic/polymer. As such, the use of only a single polymer with indicators (or otherwise) should be taken as exemplary only and not to limit the scope of the disclosure.

Figure 11:
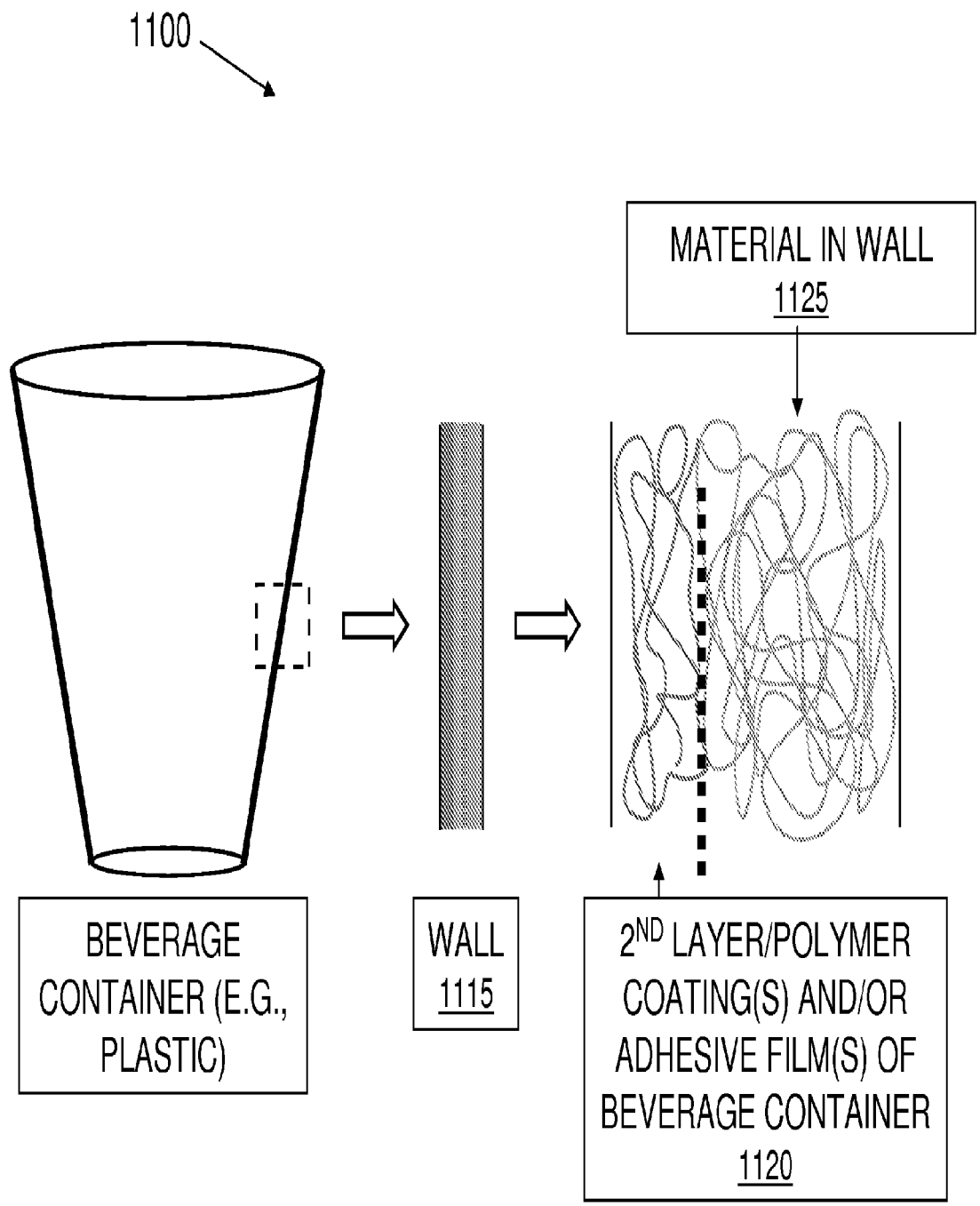
FIG. 11 is a schematic block diagram of an illustrative beverage container that may be used in accordance with one or more embodiments of the disclosure.

FIG. 11 is a schematic block diagram of an illustrative beverage container 1100 that may be used in accordance with one or more embodiments of the disclosure. According to one or more embodiments, the material of wall 1115 of the beverage container may be coated with, for example, a second material 1120 (e.g., polymer) comprising an indicator (not shown) to combine or otherwise make the material of the beverage container comprise the testing material. According to another illustrative embodiment, the material of the walls of the beverage container may be coated with, for example, a flexible adhesive film 1120 containing the indicator to make the material of the beverage container comprise the testing material. A thin layer of a polymer or co-polymer (or other appropriate material) containing the indicator may be deposited onto wall 1115. The indicator-polymer coating 1120 may be prepared at least according to any of the examples described herein (e.g., pre-attachment and/or post-attachment), however, any currently established or future established means that may enable combining the material of the beverage container with the testing material (e.g., indicators) may also be used.

As can be appreciated by those skilled in the art, incorporating indicators into the material from which the walls of the container are made, or incorporating indicators into a material that is applied as a coating to the walls of a beverage container are possible non-limiting examples of implementing the present disclosure. Thus, as used throughout, the beverage container may be considered to comprise a material (e.g., "the material of the beverage container"), whether being, e.g., a material in or of the wall of the beverage container (e.g., 720, 1125, 1325, etc.) (e.g., at any phase of the manufacturing process time of the beverage container and/or material of the beverage container), or whether being, e.g., a material (e.g., 1120, 1320, or SAM, etc.) (e.g., at any phase of the manufacturing process time of the beverage container and/or material of the beverage container) that is to be later applied/coated/layered/adhered, etc. onto the beverage container.

According to one or more alternative embodiments, different indicators may be introduced by applying a plurality of thin layers of polymer coatings 1120 that each contain the same or different indicator. Thus, the description of using a specific number of layers should be taken as exemplary only. Preferably, the over-layers of polymer coatings (i.e., coatings closer to the inner surface of the beverage container in contact with the beverage held within the beverage container) are permeable to the beverage and to the different drugs being detected in order for the drugs to penetrate to the layer/coating containing the selected corresponding indicator to maximize response of the indicator.

According to yet another embodiment, a thin plastic/polymer and/or other material (e.g., including but not limited to materials described throughout containing the indicator) may be combined or applied to the surface of a plastic/metal/glass/paper container as a flexible film with an adhesive backing. Similarly to one or more other embodiments, the flexible adhesive film need not coat the entire surface of the beverage container uniformly, and may be applied horizontally as a strip either around the inside of the container, or vertically running from top to bottom, or in any other orientations and/or patterning. Similarly to one or more other embodiments, the application of multiple adhesive films comprising different indicators or mixtures of indicators may allow testing for multiple substances (e.g., drugs, bacteria, or any other substance capable of detection).

Figure 12:
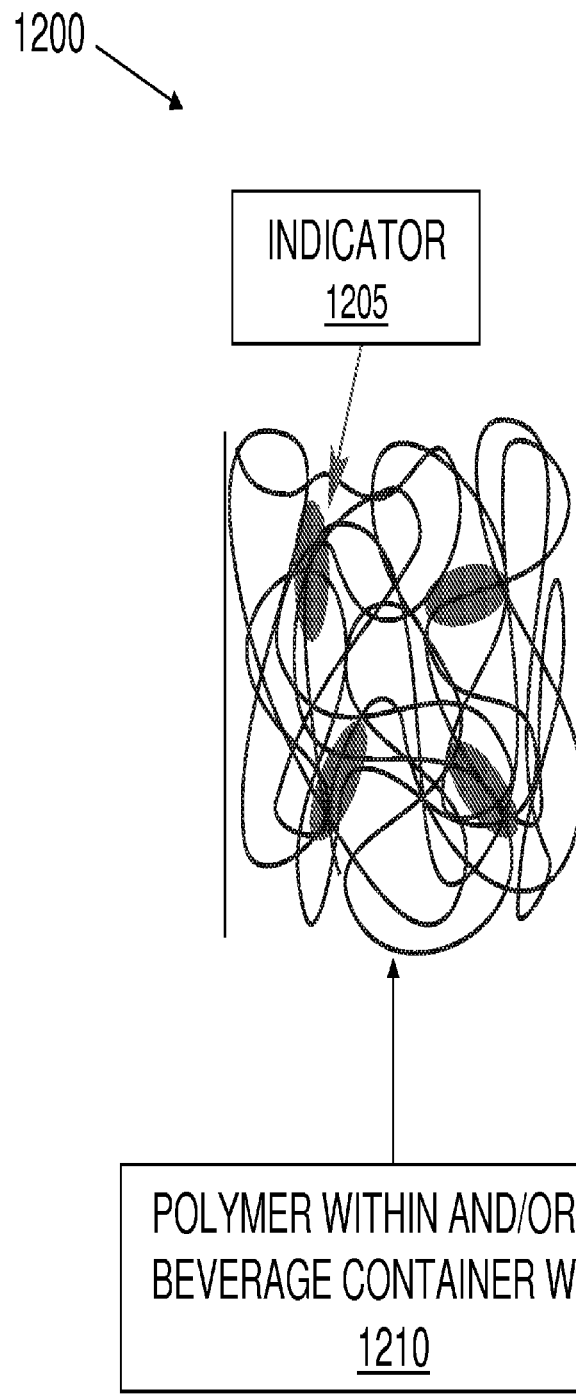
FIG. 12 is a schematic block diagram of an illustrative beverage container that may be used in accordance with one or more embodiments of the disclosure.

FIG. 12 is a schematic block diagram of an illustrative polymer 1200 comprising an embedded indicator that may be used in accordance with one or more embodiments of the disclosure. Combining by embedding an indicator within a polymer may be similar to coating the material of the beverage container wall(s) with another material (e.g., polymer layer) to which indicators are attached/combined via a chemical bond as described above. However, according to another illustrative embodiment, instead of combining by attaching the indicator via a chemical bond to the polymer material (e.g., of the beverage container wall and/or of a layered coating of the beverage container wall), the indicator 1205 is embedded within the polymer 1210. Embedding organic compounds (e.g., indicator 1205) within plastics of polymers may be achieved, for example, by forming the plastic from the polymer in the presence of the organic compound in a concentration such that the compound becomes trapped, or embedded, within the plastic as it forms. Detection of a contaminated beverage may illustratively be achieved by allowing the contaminate (e.g., drug) in the beverage (while the beverage is within the beverage container) to diffuse into the polymer coating to reach the indicator.

Depending on the size of the indicator compared to the polymer in which it is embedded, it is possible that the indicator may leach out of the polymer at some appreciable rate. However, the rate of leaching will be low or nonexistent (e.g., over the time frame for drinking one or more beverages). According to one or more alternative embodiments, leaching may be reduced or completely obviated, for example, by making the indicator larger using known techniques (e.g., attaching a material to the indicator). As a result, the indicator would still manifest a color change in the presence of the appropriate substance, but the increased size of the indicator (compared to the material within which the indicator is embedded) would prevent it from leaching through the polymer. Those skilled in the art will appreciate that any other suitable techniques for reducing and/or preventing leaching may also be used. Additionally, those skilled in the art will appreciate that other attaching/combining/incorporating techniques may also be used without departing from the scope of the disclosure. Thus, any description of any particular indicator combining technique described throughout, otherwise known currently or in the future to those skilled in the art, or combination thereof, should be taken as exemplary only and not to limit the scope of the disclosure.

Figure 13:
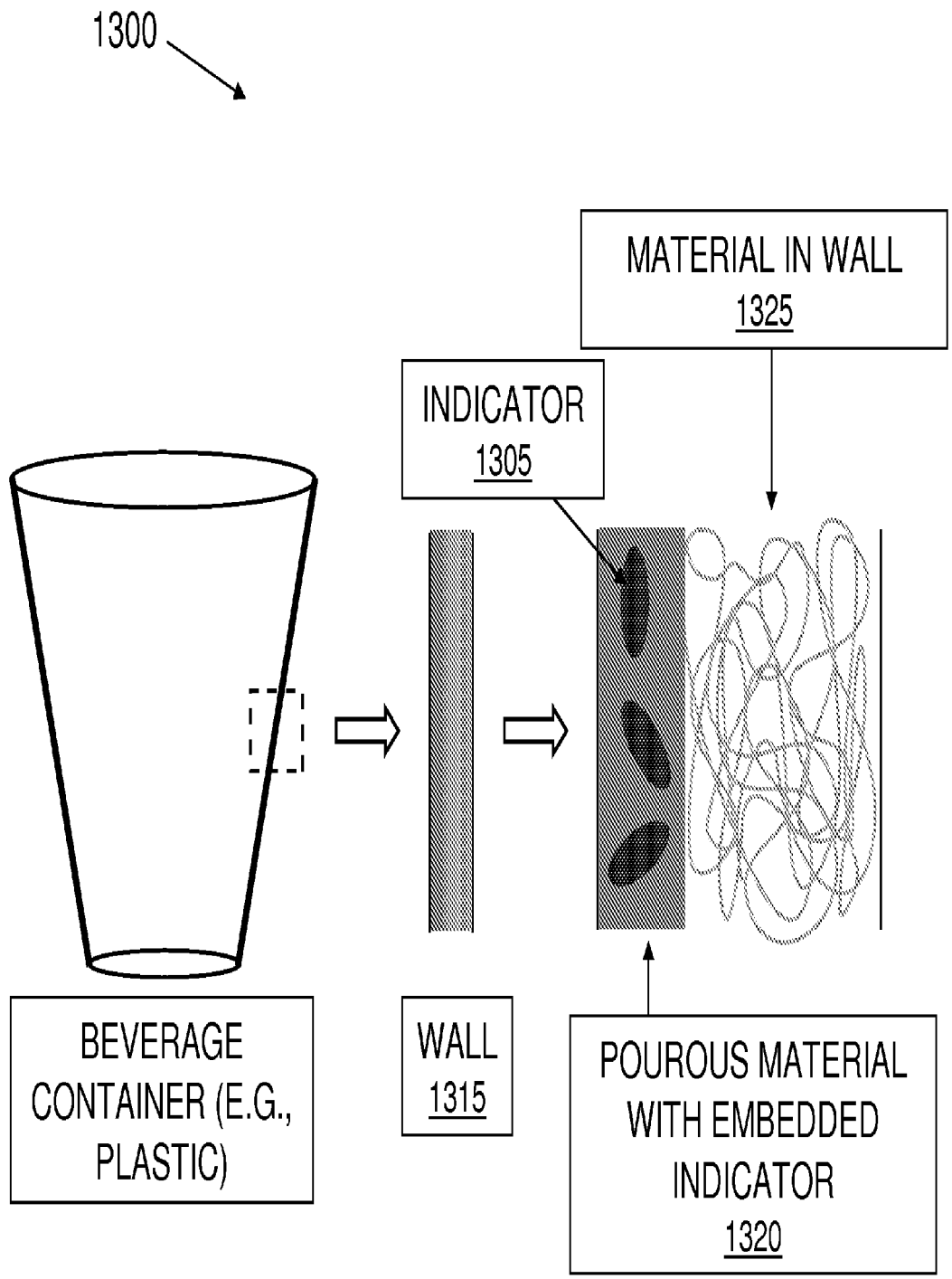
FIG. 13 is a schematic block diagram of an illustrative beverage container that may be used in accordance with one or more embodiments of the disclosure.

FIG. 13 is a schematic block diagram of an illustrative beverage container 1300 that may be used in accordance with one or more illustrative embodiments of the disclosure. According to one or more illustrative embodiments, in no particular order, an indicator 1305 may be mixed into a porous material 1320, where a thin coating of the porous material may be deposited onto the wall surface 1315 (comprising material 1325) of a, e.g., plastic/metal/glass/paper, etc., beverage container. As such, the wall surface 1315, and therefore the beverage container, may illustratively comprise material 1320. Illustratively, the porous material may be any of a variety of organic and/or inorganic materials and/or hybrid organic/inorganic materials that exhibit porous behavior such that the material (e.g., 1320) is permeated by pores or channels that allow, for example, an indicator to be incorporated within or on the surfaces of the porous material, and drug (or other contaminate) molecules contained in a beverage which is also within the beverage container) to diffuse into the pores/channels and react with the indicator 1305.

Illustratively, any type of porous material 1320 may be used to carry out the functions of the disclosure. Thus, any description of particular porous material(s) should be taken as exemplary only and not to limit the scope of the disclosure. For example, different classes of porous materials may include, but are not limited to porous synthetic polymers/copolymers, porous biopolymers (e.g., cellulose and other polymers of carbohydrates (e.g., sugars)), polymers of amino acids (e.g., proteins/enzymes), polymers of nucleic acids (e.g., DNA/RNA), porous gels (e.g., hydrogels, organogels, zerogels), porous inorganic minerals (e.g., zeolites, silica gel, nanoporous silica, mesoporous silica, microporous silica, porous glass), and porous hybrid organic/inorganic materials such as coordination polymers commonly referred to as metal-organic frameworks. Porous materials derived from combinations (mixtures) of different types of porous materials are also contemplated (e.g., zeolites embedded within or attached to the surface of a synthetic polymer). According to one or more embodiments, indicator 1305 may be chemical bonded to the chemical constituents within or on the surface of porous material 1320 (as noted above), or the indicator may be embedded/trapped within porous material 1320 (as noted above).

Described below is an example of a coating consisting of a porous material containing an indicator using porous silica. As noted above, any appropriate type of porous is material may be used to carry out the functions of the disclosure. Thus, any description of particular porous material(s) (e.g., porous silica) should be taken as exemplary only and not to limit the scope of the disclosure. Porous silica comprises silica ($SiO_2$), which is a major component in, e.g., glass and sand. Porosity in silica may result at least in part from nano-scale or micro-scale pores/channels present in the material that permeate the structure, thereby allowing solvents such as water and/or other molecules present in water to diffuse into the pores/channels within the silica. Attaching and/or embedding indicators in porous silica offer several advantages. For instance, silica is cheap, easy to work with, forms thin films easily (e.g., TLC plates), may be dispersed as porous particles in polymers to form flexible films, and forms pores/channels that are very permeable to water and other aqueous solutions.

Notably, the chemical structures, physical properties, level of porosity, mechanical stability, etc. of porous silica may vary considerably. For example, crystalline porous silica with properties similar to glass would be more appropriate for bonding well to glass containers. Softer, more flexible films of porous silica particles dispersed in polymers or elastomers (e.g., rubbery gel materials) would be more appropriate for bonding well to plastic containers. As such, depending at least on such things as the material of the beverage container, a preferred porous material may be selected. As with the embodiments described throughout, porous silica and/or films containing porous silica may be applied uniformly to the surface of the beverage container and/or patterned on the surface in specific locations.

Figure 14:
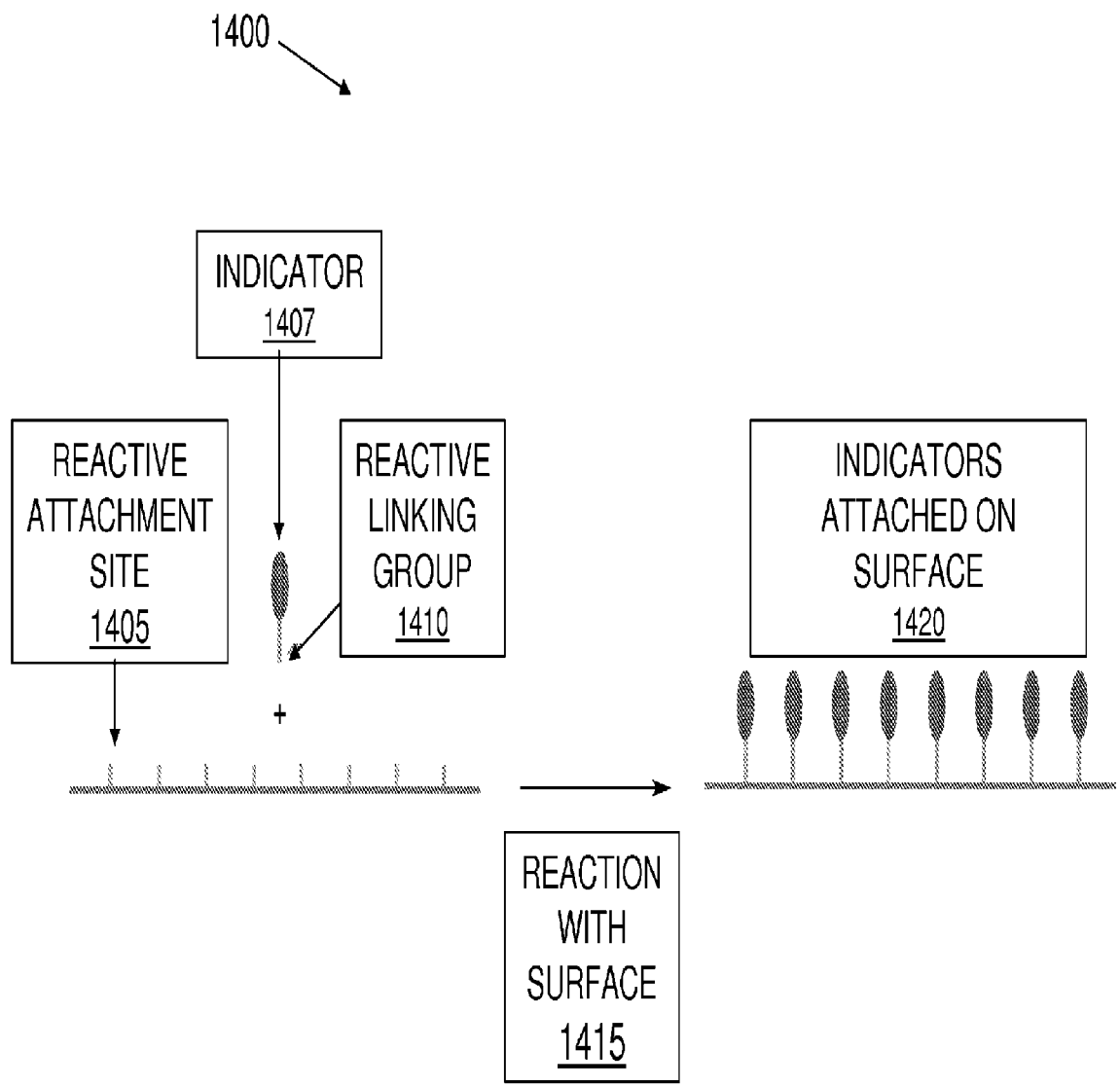
FIG. 14 is a schematic block diagram showing an exemplary technique/procedure for attaching indicators to the surface of a beverage container that may be used in accordance with one or more embodiments of the disclosure.

According to one or more alternative embodiments, indicators may be directly attached (e.g., secured, affixed, coupled, combined, incorporated, etc.) to a surface of the beverage container, e.g., as self-assembled monolayers (SAMs) and/or as thin films. FIG. 14 is a schematic block diagram showing an exemplary technique/procedure 1400 for attaching indicators 1407 to the surface of, e.g., metal, glass, plastic or paper beverage container via chemical bonding between a reactive linking group 1410 and an attachment site 1405 on the surface (e.g., of the beverage container) according to one or more embodiments of the disclosure. Attachment site(s) 1405 on the surface illustratively represent an atom or group of atoms (e.g., in the case of a metal) or a chemical group (e.g., in the case of glass, plastic, and/or paper) that form a chemical bond with reactive linking group 1410 on indicator 1407. FIG. 14 may differ from one or more embodiments described throughout, for instance, as it involves attaching indicators directly to the surface of a metal (e.g., gold, silver, etc.), a silica (e.g., glass), a polymer (e.g., plastic or otherwise), and/or a paper material, etc. of a beverage container. Those skilled in the art will recognize that the implementation of SAMs is well known and may be implemented using any currently established or future established means, such as the illustrative examples described further below. Therefore, any specific implementations of SAMs described should be taken as exemplary only and not to limit the scope of the disclosure. Generally, however, the process comprises an indicator 1407 with a linking group 1410 that will attach to the surface by forming a chemical bond (described above) or any other chemical bond/reaction with the surface 1415 that results in attachment of indicator 1407 to the surface of, e.g., metal, glass, plastic and/or paper as illustratively represented by 1420. That process is referred to as self-assembly and the resulting molecular film is referred to as a self-assembled monolayer, or SAM.

The term SAM generally refers to a molecular film that is a monolayer the thickness of, e.g., a single molecule. In some cases, however, the above process results in a multi-layer thin film that is the thickness of, e.g., two or more molecules (e.g., a bilayer, a trilayer, etc.). Multilayer films generally form when there is a strong attractive interaction (e.g., an intermolecular bond) between the portions of the molecules exposed on the surface of the SAM. As a result, additional layers may be able to bind on top of the first layer (i.e., the SAM). For example, the naturally occurring amino acid cysteine is known to form bilayers rather than monolayers when cysteine is exposed to gold surfaces. In the case of cysteine, the "overlayer", or $2^{nd}$ layer, may form because there is a strong attraction between the amino and acid organic groups in cysteine that cause a second layer to stick on the first layer. The result is a bilayer in which the first layer (i.e., the SAM) anchors the molecules firmly to the gold surface by forming a strong chemical bond; weak attractions between the surface and molecules in solution may cause a second layer to attach on top of the first. As a consequence, according to one or more illustrative embodiments, direct attachment of indicators to create SAMs may result either in a SAM (a monolayer) of attached indicators, or a bilayer or multilayer composed of two or more layers of attached indicators. Typically, a SAM is a monolayer and as such direct attachment of indicators to surfaces may be referred to as forming thin films. However, the term SAM (or thin film) may be interpreted to encompass either monolayers (SAMs), bilayers, other multilayer films, or any combination thereof.

As with one or more of the illustrative embodiments described throughout, SAMs may be applied uniformly to the surface of the beverage container and/or patterned on the surface in specific locations, e.g., by applying them with a roller, a stamp coated with a solution of the indicator, or by spraying them onto the surface (e.g., ink jet printing). Illustratively, the application of an indicator with a roller or via spraying will do the same thing by patterning the indicator in the region on the surface in contact with the roller or under the nozzle of the sprayer. Illustratively, molecules that are desired to be positioned on surfaces with precise control may be patterned using microcontact printing, a technique developed by George Whitesides.

Figure 15:
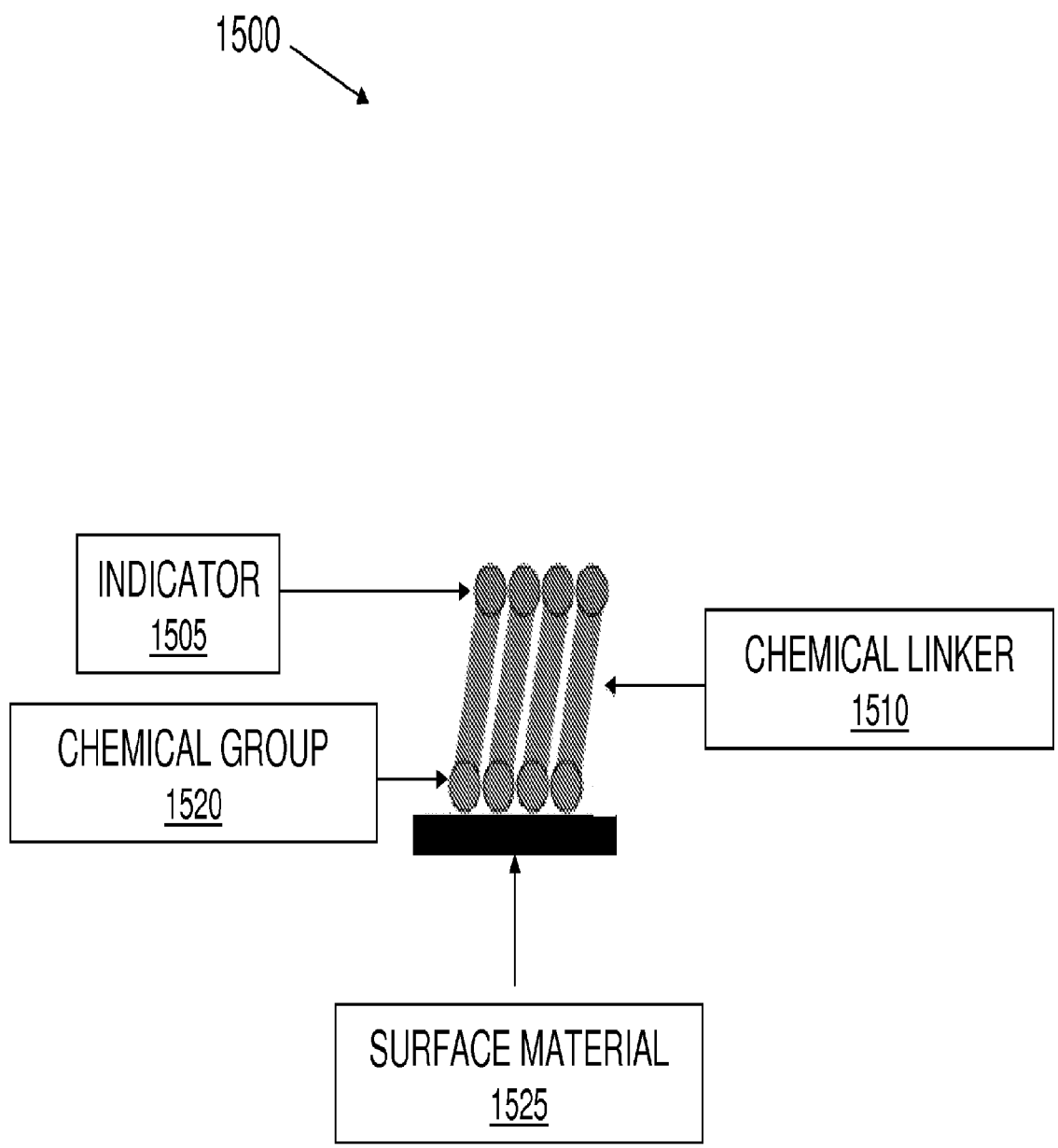
FIG. 15 is a schematic block diagram showing an exemplary SAM on a material that may be used in accordance with one or more embodiments of the disclosure.

FIG. 15 is a schematic block diagram showing an exemplary SAM 1500 on a material 1525 (e.g., metal, glass, plastic, paper, etc.), where the SAM illustratively comprises an indicator 1505, chemical linker 1510 (e.g., hydrocarbon group), and (reactive) chemical group 1520 according to one or more embodiments of the disclosure.

An example of SAMs on gold is described below. However, those skilled in the art will appreciate that other metals with similar properties (e.g., silver, copper, etc.) may also be used. As such, the description of creating a SAM on any particular surface material 1525 (e.g., gold) should be taken as illustrative only and not to limit the scope of the disclosure. Illustratively, virtually any organic molecule that contains an exposed chemical group 1520, such as a sulfur-containing group (e.g., a thiol (SH) or a disulfide) may spontaneously bond to the surface of gold. Upon exposure to the gold surface, the sulfur-containing molecules may bind to the gold surface and may then form a uniform layer of molecules covering the gold surface that is the thickness of, e.g., a single molecule as it stands up from the surface. For example, dipping a gold-coated glass microscope slide into a solution of a thiol may produce a thin film of molecules attached to the gold surface via a gold-sulfur chemical bond. SAMs may be used as a means to attach a variety of different types of molecules (e.g., small organic molecules, proteins, DNA, polymers, sugars, etc.) to gold surfaces. Those skilled in the art will recognize that SAMs may be utilized to modify the surface properties of materials and for applications that may require attachment of molecules to surfaces. For example, SAMs may be used to attach and pattern biomolecules such as DNA on gold in order to create a "lab on a chip". SAMs may also be used to pattern ion-selective organic molecules on gold in microfluidic devices to create sensors for blood analytes. Only a very thin layer (e.g., 0.1-100 nanometers thick) of gold may be required on the surface, and therefore is not cost prohibitive. Gold surfaces for making SAMs, generally, may be prepared by evaporating or plating a small amount of gold onto glass or silicon, as well as a wide variety of other known and suitable substrates. Attachment of indicator 1505 to a gold surface may require the presence of a (reactive) sulfur-containing group 1520 on the indicator. Sulfur-containing groups may be introduced onto indicator 1505 using known methods of organic synthesis. Gold generally is not transparent and may not bond well to other materials such as glass or plastic. However, if a thin enough layer of gold (e.g., less than 100 angstroms, or 0.1 nanometers) is applied, however, gold may become optically transparent. Moreover, adhesion of gold films on materials it does not stick (i.e., bond) well to may be improved by applying a thin layer of another metal, such as titanium or chromium, and then applying gold onto that metal.

An example of SAMs on glass is described below. However, those skilled in the art will appreciate that other materials with similar properties may also be used. As such, the description of creating a SAM on any particular surface material 1525 (e.g., glass) should be taken as illustrative only and not to limit the scope of the disclosure. Similar to the concept of SAMs of molecules (e.g., indicators) on gold, a similar concept may be applied on glass surfaces. For example, molecules with one or more reactive silanesilyl groups (groups such as trihalogenated silanes or trialkoxysilanes that contain reactive silicon atoms) may "spontaneously" form, e.g., a silicon-oxygen chemical bond to the glass surface such that the glass becomes covered with a "thin layer" (e.g., a monolayer one molecule in thickness) of the molecules. SAMs on glass are less costly to prepare and have the advantage that glass, and thus the SAM, is transparent. According to one or more embodiments, SAMs of indicators on glass are preferred for attaching indicators to glass beverage containers.

An example of SAMs on plastic is described below. However, those skilled in the art will appreciate that other materials with similar properties may also be used. As such, the description of creating a SAM on any particular surface material 1525 (e.g., plastic) should be taken as illustrative only and not to limit the scope of the disclosure. SAMs of molecules (e.g., indicators) on plastics is similar to the principle for SAMs on gold and glass surfaces. For example, formation of a SAM on plastic may require that the polymer of the plastic contain one or more surface-exposed reactive groups and that the molecule to be attached contain one or more reactive groups that may form a chemical bond with the reactive groups on the plastic.

An example of SAMs on paper is described below. However, those skilled in the art will appreciate that other materials with similar properties may also be used. As such, the description of creating a SAM on any particular surface material 1525 (e.g., paper) should be taken as illustrative only and not to limit the scope of the disclosure. SAMs of molecules (e.g., indicators) on paper, or cellulose is similar to the principle for SAMs on glass and plastic surfaces. For example, formation of a SAM on paper may require that cellulose or other chemical constituents of the paper contain one or more surface-exposed reactive groups and that the molecule to be attached contain one or more reactive groups that may form a chemical bond with the reactive groups on the paper. A major chemical component in paper is cellulose, which is a biopolymer composed of the sugar glucose. Glucose contains many alcohol (OH, or hydroxyl) groups similar to the surface of glass. Therefore, molecules with reactive groups that form a chemical bond to the surface of glass (as noted above) may also form a chemical bond to the cellulose in paper.

Direct attachment of indicators onto metal, glass, plastic, and paper surfaces potentially offers advantages compared to other illustrative embodiments described throughout. For example, in no particular order, those advantages are: (1) no polymer or gel coating is required; (2) very small amounts of indicator are required to form SAMs; and (3) application of molecule/indicators can be controlled spatially on the surface more easily, e.g., using a well-known "stamping" technique or other suitable technique. In a preferred embodiment using a SAM, the indicator has a high sensitivity and corresponding response that can be more easily observed by the human eye.

Due at least to various "quality control" purposes known to those skilled in the art, any of the above noted processes (or other processes) of making the material of the beverage container comprise the testing material preferably would not be carried out by an "individual" end user (e.g., individual, proprietor in a drinking establishment, etc.), but rather by, e.g., a manufacturing/laboratory process or the like. However, it is contemplated that one or more of the techniques described throughout may be performed (i.e., implemented) as an extension of one or more illustrative embodiments described above, by the end user given the appropriate equipment and instruction. For example, the end users may purchase a "spray", which may illustratively comprise either a pure liquid indicator and/or a solution of the indicator dissolved in a suitable solvent. The end user may also purchase an applicator, such as a spraying apparatus, designed to deliver the spray to the appropriate beverage container. Those skilled in the art will appreciate that any suitable applicator apparatus known to those skilled in the art and/or described throughout, that may be capable of delivering the spray (e.g., pure liquid indicator and/or a solution of the indicator dissolved in a suitable solvent) may also be used. Thus, the delivery of the indicator/solution need not actually be delivered literally in spray form. According to one or more embodiments, the applicator apparatus may comprise a pump-action bottle featuring a button, handle, bulb, dropper, etc. that the user may operate manually, such as, a spray device containing a compressed gas, or a spray bottle featuring a mechanical/electrical spraying mechanism, etc.

According to one or more illustrative embodiments, in the case of a pure liquid indicator, the indicator may be delivered by the spray to the surface as a substantially pure substance such that a small percentage of the indicator binds to the surface (i.e., the surface becomes saturated with bound indicator) leaving the majority of the indicator unbound as a residue on the surface. The residual indicator may then be rinsed off or inactivated upon contact with the beverage. According to one or more illustrative embodiments, in the case of an indicator dissolved in a suitable solvent, the indicator may be delivered by the spray to the surface as a mixture of indicator and solvent (e.g., water, or other solvent) such that a (small) percentage of the indicator binds to the surface leaving the majority of the indicator and the solvent unbound as a residue on the surface. Application of the indicator either as a pure liquid or as a solution will result in formation of a thin film of indicator on the surface, leaving residual indicator unbound on the surface (as well as solvent if a solution is used).

According to one or more alternative embodiments, an indicator may be contained in a "dishwasher tablet" (e.g., bag/pouch) means and/or "dishwasher additive" means (or the like), such as the kind conventionally used in dishwashers to clean dishes. For example, the Cascade dishwasher pouch design offered by Procter & Gamble may be altered to contain the indicator for later application. As such, the process(es) of making the material of the beverage container comprise the indicator testing material may be accomplished, e.g., by the end user, by "washing" the beverage container in a dishwasher in the presence of the tablet or additive. According to one or more illustrative embodiments, the tablet and/or additive containing the indicator with a reactive chemical group may be placed in the receptacle in a dishwasher where detergent or other additives normally are placed (or any other suitable location). Upon starting the dishwasher, water enters the dishwasher and the tablet/additive is released or exposed to the water. The tablet/additive then dissolves into the water to form a solution of additive in water. The solution of additive in water is then applied to the surface of the beverage container through the normal spraying and agitation process of the dishwasher. When the solution of indicator comes into contact with the surface of the beverage container, it reacts with the material of the beverage container and forms a chemical bond on the surface or is absorbed. Advantageously, the dishwasher provides the water to form an aqueous solution of the indicator contained in the tablet/additive, and also provides the spraying/agitating action that applies the solution to the surface of the beverage containers in the dishwasher. Another illustrative advantage to using a dishwasher (or machine with the similar relevant functions) is that most if not all residual indicator that does not bind to or is absorbed by beverage containers may be removed during the rinse cycle of the dishwasher. Alternatively, due at least to the reason discussed below, it may be advantageous to have a machine with similar functionality of a dishwasher, but that does not always use water. As another illustrative alternative embodiment, a dishwasher may comprise an "indicator" cycle, where a suitable solvent is introduced instead of water, and where water is used, e.g., only for the final rinse cycle.

As noted above, dishwashers generally involve the use of water. The indicator may not bind to the beverage container if the reactive chemical group in the indicator reacts with water. For example, attachment of organic compounds to glass may require the use of one or more trihalosilyl or trialkoxysilyl groups to form a chemical bond to the surface of glass. Those reactive chemical groups may react with water as well as, e.g., glass, since water is similar in reactivity to the alcohol groups exposed on the surface of glass. As a consequence, indicators with those reactive chemical groups may react with water when the tablet/additive dissolves. Trihalosilyl groups in particular are very sensitive to the presence of water. Nevertheless, it may still be possible to apply an indicator to glass containers in the presence of water. For example, trialkoxylsilyl groups generally react more slowly with water compared to trihalosilyl groups. Some of the indicator may then react with the glass containers as well as with water if a sufficiently high concentration of indicator is present and delivered by the tablet/additive. Moreover, only a very small amount of indicator is required to fully cover the surface of a beverage container. Thus, even if less than, e.g., 1% of the indicator reaches the surface, that may be sufficient to coat the entire surface of the container. This same issue may hold true for other reactive chemical groups necessary for form a chemical bond to other container materials such as metal, paper, plastic, etc. It may be necessary to use indicators with reactive chemical groups that are compatible with water in order to apply indicators to containers in a dishwasher setting.

While one or more embodiments may be described in terms of a polymer, those skilled in the art will recognize that any other appropriate material may also be used without departing from the scope of the disclosure. Furthermore, as can be appreciated by those skilled in the art, a polymer need not necessarily be referred to exclusively as a plastic, but may also encompass a large class comprising both natural and synthetic materials with a wide variety of properties. Furthermore, while one or more embodiments may be described in terms of a general polymer, those skilled in the art will recognize that any suitable polymer (e.g., metal-organic frameworks (MOFs), branched polymers such as star polymers, comb polymers, brush polymers, dendronized polymers, ladders, and dendrimers, etc.) may also be used without departing from the scope of the disclosure. As such, any particular description of using a particular material (e.g., gel, metal, paper, polymer, linear, non-linear, hybrids, etc., or otherwise), should be taken as exemplary only and not to limit the scope of the disclosure.

While one or more illustrative embodiments are disclosed as testing for drugs (e.g., Rohypnol, Ketamine, GHB, etc.), those skilled in the art will appreciate that the present disclosure may also be used to detect other substances (i.e., contaminates) in a beverage container or otherwise. For example, detection of organisms may also be used to determine if a beverage (e.g., drinking water) is safe (e.g., if dangerous microorganisms are present). Generally, in the case of an organism, for example, the cell surface of the organism may act similarly to a drug. The appropriate indicator, for example, protein, antibody, chemical indicator, DNA, RNA, sugar, fatty acid, etc. may be selected that recognizes the cell surface of the specific organism. Alternatively, for example, if the organism releases/secretes a waste product, chemical signal, or other chemicals that can be recognized by an indicator, those compounds similarly may be monitored. Some organisms secrete chemicals that enable them to bind to different types of surfaces, which may also be monitored. Moreover, cranberry juice may either prevent the organisms from sticking to surfaces or actually kill them. However, in the case where a compound that did the opposite (i.e., to which they were attracted or stuck to), the organism may also be detectable with an indicator.

Advantageously, by using the beverage container itself as the testing material, the user is provided with a (near) effortless and continuous monitoring of the beverage within the beverage container without such illustrative burdens required by the prior art, such as, inter alia, remembering to bring a testing kit (disguised or otherwise) with a sufficient number of testing strips, remembering to test the beverage, and remembering to re-test the beverage at different times. As another advantage, even if the user cannot distinguish between the effect of the alcohol and the effect of ingesting a contaminated beverage, other onlookers may still notice the reaction of the beverage container/testing material and provide a warning to the user. Additionally, the testing material of the beverage container (e.g., any unused portions) may also be used to test other beverages of different users, such as an acquaintance that may not be in possession of the disclosed beverage container or a testing kit.

While there have been shown and described illustrative embodiments using a beverage container, it is to be understood that various other adaptations and modifications may be made within the spirit and scope of the present invention. For example, the embodiments have been shown and described herein where the wax film protecting the testing material prevents the beverage contained within the beverage container from immediately contacting and reacting with the testing material lined with the beverage container. However, the embodiments of the invention in their broader sense are not so limited, and may, in fact, be advantageously used to line, e.g., a beverage stirrer or a beverage straw. For example, the straw may be lined with the testing material and the wax. This would allow the straw to function as both a conventional straw and as the testing material to attain some or all of above advantages.

The foregoing description has been directed to specific embodiments of this disclosure. It will be apparent, however, that other variations, substitutions, combinations, and modifications may be made to the described embodiments, with the attainment of some or all of their advantages. For instance, it is expressly contemplated that the components and/or elements described herein may vary without departing from the true spirit and scope of the invention. For example, while specific types of drug testing materials have been discussed, any drug testing method, device or material suitable for use in the disclosure is contemplated. Additionally, while only a few drugs have been described for detection, it is contemplated that other drugs and substances, such as caffeine or alcohol, may also be detected using an appropriate testing material. Additionally, different film material other than wax that is suitable for use in the disclosure is contemplated. Additionally, different locations of the testing material are also contemplated. For example, the entire beverage container (or at least a portion thereof) exclusively may be the testing material shaped as a beverage container. Accordingly, this description is to be taken only by way of example and not to otherwise limit the scope of the invention. Therefore, it is the object of the appended claims to cover all such variations and modifications as come within the true spirit and scope of the invention.

What is claimed is:

1. An apparatus configured to detect a contaminated beverage, comprising:
   a beverage container configured to hold a beverage, wherein the beverage container comprises a material; and
   an indicator chemically bonded to at least a portion of the material of the beverage container, the indicator configured to visibly react when the indicator is contacted with a date rape drug in the beverage to indicate the date rape drug is present in the beverage, wherein at least portion of the material of the beverage container comprises the indicator, and wherein the visible reaction is shown on at least the portion of the material of the beverage container via the indicator chemically bonded to at least the portion of the material of the beverage container.

2. The apparatus of claim 1 wherein the indicator is pre-attached to at least the portion of the material of the beverage container.

3. The apparatus of claim 1 wherein the indicator is post-attached to at least the portion of the material of the beverage container.

4. The apparatus of claim 1 wherein the indicator is chemically bonded to a monomer of a polymer of at least the portion of the material of the beverage container.

5. The apparatus of claim 1 wherein the indicator is chemically bonded to a monomer of a co-polymer of at least the portion of the material of the beverage container.

6. The apparatus of claim 1 wherein the indicator is chemically bonded as a self-assembled monolayer (SAM) to at least the portion of the material of the beverage container.

7. The apparatus of claim 1 wherein at least the portion of the material of the beverage container comprises a second material, and wherein the indicator is chemically bonded to at least a portion of the second material.

8. The apparatus of claim 1 wherein the indicator is patterned on at least the portion of the material of the beverage container.

9. The apparatus of claim 1 wherein the date rape drug includes at least one of benzodiazepine, ketamine, Gamma-Hydroxybutyrate, Gamma Butyrolactone, and 1,4-butananediol.

10. The apparatus of claim 1 wherein at least the portion of the material of the beverage container comprises a film, and wherein the film comprises the chemically bonded indicator.

11. The apparatus of claim 1 wherein the indicator comprises at least one of a protein indicator, an antibody indicator, a chemical indicator, a DNA indicator, a RNA indicator, a sugar indicator, a caffeine indicator, a fatty acid indicator, a waste product indicator, and an alcohol indicator.

12. The apparatus of claim 1 wherein the beverage container comprises at least one of a straw and a stirrer.

13. The apparatus of claim 1 wherein the beverage container comprises at least one of a cup, a glass, a mug, a can, and a bottle.

14. A method for producing an apparatus configured to test a beverage for one or more date rape drugs, comprising:
   selecting an indicator that shows a visible reaction when contacted with a date rape drug in the beverage; and
   introducing, by chemical bonding, the selected indicator to at least a portion of a beverage container, wherein the visible reaction is shown by at least the portion of the beverage container via the selected indicator when the date rape drug in the beverage is contacted with the selected indicator introduced to at least the portion of the beverage container.

15. The method of claim 14 wherein introducing the selected indicator to at least the portion of the beverage container by chemical bonding comprises post-attaching the selected indicator to at least the portion of the beverage container.

16. The method of claim 14 wherein the selected indicator is chemically bonded to a monomer of a polymer of at least the portion of the beverage container.

17. The method of claim 14 wherein the selected indicator is chemically bonded to a monomer of a co-polymer of at least the portion of the beverage container.

18. The method of claim 14 wherein the selected indicator is chemically bonded as a self-assembled monolayer (SAM) to at least the portion of the beverage container.

19. The method of claim 14 wherein introducing the selected indicator to at least the portion of the beverage container by chemical bonding comprises pre-attaching the selected indicator to at least the portion of the beverage container.

20. The method of claim 14 wherein the selected indicator is patterned on at least the portion of the beverage container.

21. The method of claim 14 wherein the selected indicator is introduced by a machine with an additive added to the machine.

22. The method of claim 21 wherein the machine comprises a dishwasher.

23. The method of claim 14 wherein the date rape drug includes at least one of benzodiazepine, ketamine, Gamma-Hydroxybutyrate, Gamma Butyrolactone, and 1,4-butananediol.

24. The method of claim 14 wherein introducing the selected indicator to at least the portion of the beverage container by chemical bonding comprises at least one spraying, dipping, rolling, stamping, printing, and evaporating.

25. The method of claim 14 wherein introducing the selected indicator to at least the portion of the beverage container by chemical bonding comprises applying a film to at least the portion of the beverage container, wherein the film comprises the chemically bonded indicator.

26. The method of claim 14 wherein the selected indicator comprises at least one of a protein indicator, an antibody indicator, a chemical indicator, a DNA indicator, a RNA indicator, a sugar indicator, a caffeine indicator, a fatty acid indicator, a waste product indicator, and an alcohol indicator.

27. The method of claim 14 wherein the beverage container comprises at least one of a straw and a stirrer.

28. The method of claim 14 wherein the beverage container comprises at least one of a cup, a glass, a mug, a can, and a bottle.

* * * * *

UNITED STATES PATENT AND TRADEMARK OFFICE
CERTIFICATE OF CORRECTION

| | |
|---|---|
| PATENT NO. | : 8,834,946 B2 |
| APPLICATION NO. | : 13/404663 |
| DATED | : September 16, 2014 |
| INVENTOR(S) | : Michael T. Abramson et al. |

Page 1 of 1

It is certified that error appears in the above-identified patent and that said Letters Patent is hereby corrected as shown below:

In the claims

At column 29, claim 1, line 14, after "at least" and before "portion", please insert --the--

Signed and Sealed this
Eighteenth Day of November, 2014

Michelle K. Lee
*Deputy Director of the United States Patent and Trademark Office*